(12) United States Patent
Janowski et al.

(10) Patent No.: US 6,860,883 B2
(45) Date of Patent: Mar. 1, 2005

(54) EXTERNAL FIXATION APPARATUS AND METHOD

(75) Inventors: Brian P. Janowski, Marquette, MI (US); Jeffrey L. Trudeau, Marquette, MI (US)

(73) Assignee: Pioneer Laboratories, Inc., Marquette, MI (US)

(*) Notice: Subject to any disclaimer, the term of this patent is extended or adjusted under 35 U.S.C. 154(b) by 87 days.

(21) Appl. No.: 10/074,607

(22) Filed: Feb. 11, 2002

(65) Prior Publication Data

US 2003/0153910 A1 Aug. 14, 2003

(51) Int. Cl.[7] .................................................. A61F 5/04
(52) U.S. Cl. .......................................... 606/56; 606/59
(58) Field of Search .............................. 606/53, 56, 54, 606/55, 57, 58, 59

(56) References Cited

U.S. PATENT DOCUMENTS

| | | |
|---|---|---|
| 1,398,842 A | 11/1921 | Cruse |
| 2,494,792 A | 1/1950 | Bloom |
| 2,966,383 A | 12/1960 | Boetcker et al. |
| 3,072,118 A | 1/1963 | Standerwick et al. |
| 3,336,922 A | 8/1967 | Taylor |
| 3,391,693 A | 7/1968 | Georgiade et al. |
| 3,604,412 A | 9/1971 | Gardner |
| 3,654,923 A | 4/1972 | Crutchfield |
| 3,669,102 A | 6/1972 | Harris |
| 3,867,932 A | 2/1975 | Huene |
| 3,923,046 A | 12/1975 | Heifetz |
| 4,308,863 A | 1/1982 | Fischer |
| 4,361,144 A | 11/1982 | Slätis et al. |
| 4,365,624 A | 12/1982 | Jacquet |
| 4,393,868 A | 7/1983 | Teague |

(List continued on next page.)

FOREIGN PATENT DOCUMENTS

| | | |
|---|---|---|
| DE | 33/02/078 C2 | 4/1988 |
| DE | 41 20 393 C1 | 6/1992 |
| FR | 752676 | 9/1933 |

*Primary Examiner*—Pedro Philogene
*Assistant Examiner*—David Bonderer
(74) *Attorney, Agent, or Firm*—Fitch, Even, Tabin & Flannery

(57) ABSTRACT

A bone fixation apparatus and method are provided that allow a user to push bone pins into engagement with bones with more precision and accurate feel as to proper engagement and the clamping forces between the pins and bone over prior devices utilizing applicator guns and the like. Fine tuning of the clamping forces is also contemplated. Compact and highly ergonomic bone fixators are provided which allow the user to remain close to the pin application site during clamping of the pins onto the bone. Significant flexiblity is preferably incorporated by having two adjustably connected positioner bodies which can each mount a pin holder module releasably attached thereto. A fixation system with improved rigidity is also provided by way of independent clamping members for each of a pair of rod mounts on each pin positioner. The independent clamp members keeps their size to a minimum while allowing the angular separation of connecting rods secured in the rod mounts and spanning and interconnecting two fixators to be optimized, e.g. approximately eighty degree angular spacing, from a system stability standpoint.

23 Claims, 28 Drawing Sheets

U.S. PATENT DOCUMENTS

| | | | |
|---|---|---|---|
| 4,444,179 A | 4/1984 | Trippi | |
| 4,450,834 A | 5/1984 | Fischer | |
| 4,584,995 A | 4/1986 | Koeneman | |
| 4,612,930 A | 9/1986 | Bremer | |
| 4,667,660 A | 5/1987 | Eingorn | |
| 4,838,264 A | 6/1989 | Bremer et al. | |
| 4,895,141 A | 1/1990 | Koeneman et al. | |
| 5,010,881 A | 4/1991 | Boudreau et al. | |
| 5,042,462 A | 8/1991 | Bremer | |
| 5,122,132 A | 6/1992 | Bremer | |
| 5,122,140 A | 6/1992 | Asche et al. | |
| 5,156,588 A | 10/1992 | Marcune et al. | |
| 5,196,012 A | 3/1993 | Malka | |
| 5,197,965 A | 3/1993 | Cherry et al. | |
| 5,300,071 A * | 4/1994 | Browner et al. | 606/57 |
| 5,312,403 A | 5/1994 | Frigg | |
| 5,312,412 A * | 5/1994 | Whipple | 606/96 |
| 5,347,894 A | 9/1994 | Fischer | |
| 5,354,300 A * | 10/1994 | Goble et al. | 606/80 |
| 5,372,597 A * | 12/1994 | Hotchkiss et al. | 606/56 |
| 5,431,659 A | 7/1995 | Ross, Jr. et al. | |
| 5,443,464 A | 8/1995 | Russell et al. | |
| 5,522,817 A | 6/1996 | Sander et al. | |
| 5,537,704 A | 7/1996 | Dinkler | |
| 5,578,032 A | 11/1996 | Lalonde | |
| 5,613,971 A * | 3/1997 | Lower et al. | 606/96 |
| 5,628,752 A * | 5/1997 | Asnis et al. | 606/104 |
| 5,674,186 A | 10/1997 | Guigui et al. | |
| 5,961,528 A | 10/1999 | Birk et al. | |
| 6,017,341 A | 1/2000 | Windhagen et al. | |
| 6,030,387 A | 2/2000 | Ballier | |
| 6,030,402 A * | 2/2000 | Thompson et al. | 606/185 |
| 6,159,210 A | 12/2000 | Voor | |
| 6,179,846 B1 | 1/2001 | McFadden | |
| 6,283,965 B1 | 9/2001 | Ballier | |
| 6,355,037 B1 * | 3/2002 | Crosslin et al. | 606/57 |
| 6,428,540 B1 * | 8/2002 | Claes et al. | 606/53 |
| 2001/0051806 A1 * | 12/2001 | Ballier | 606/54 |

* cited by examiner

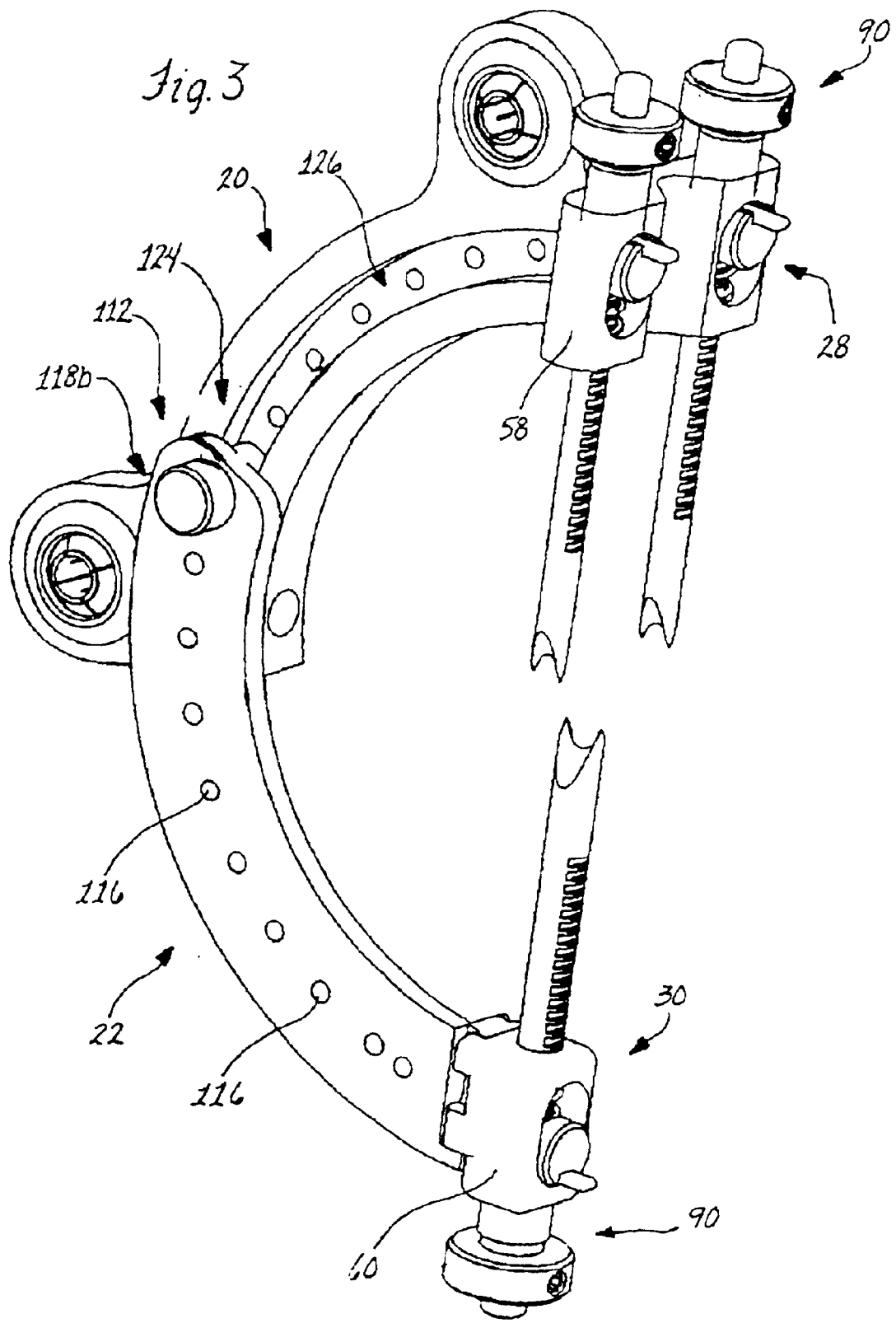

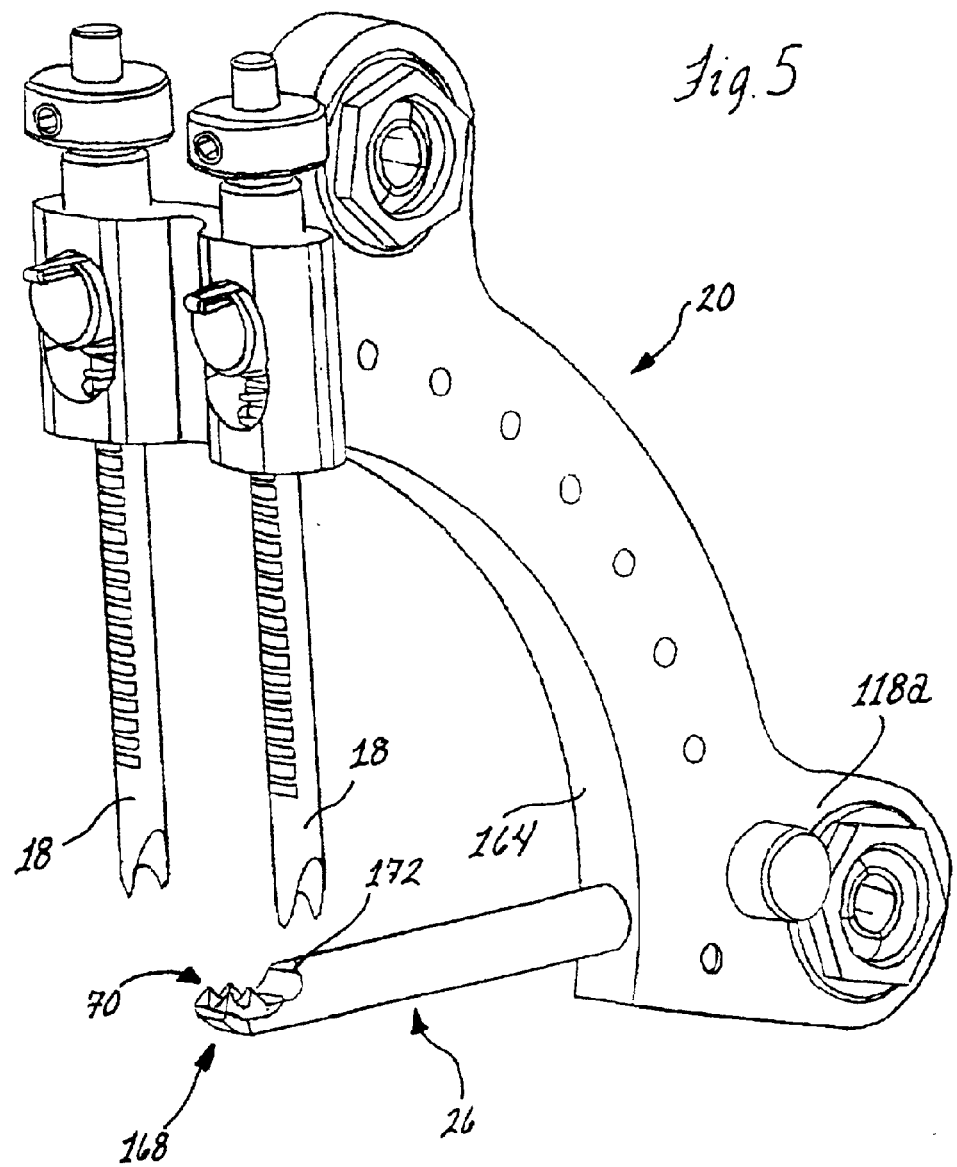

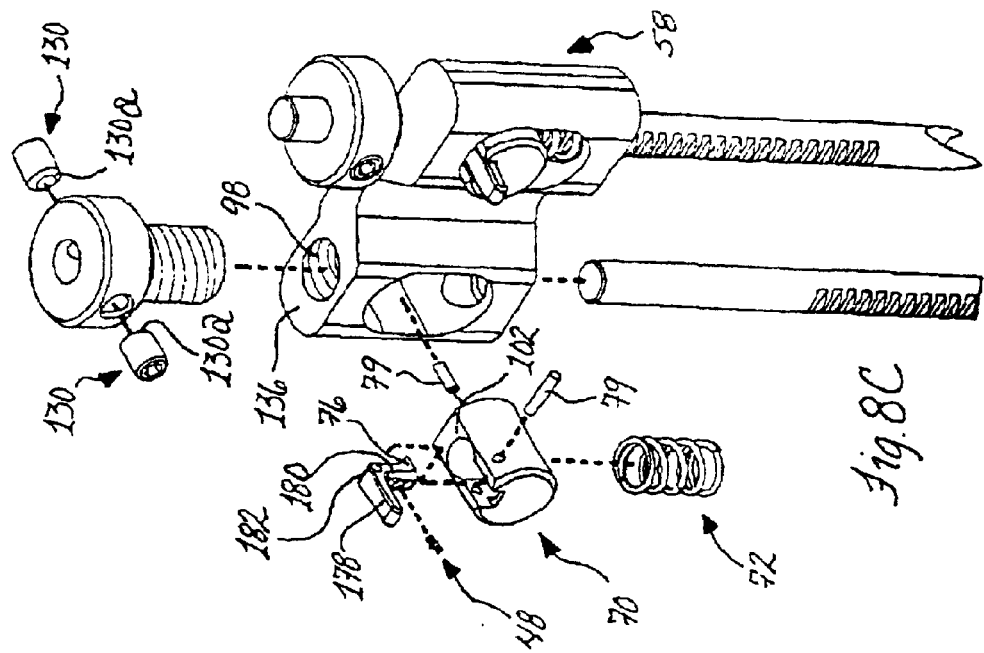
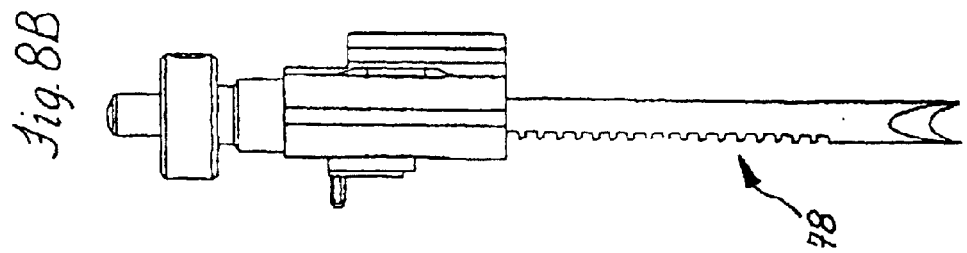
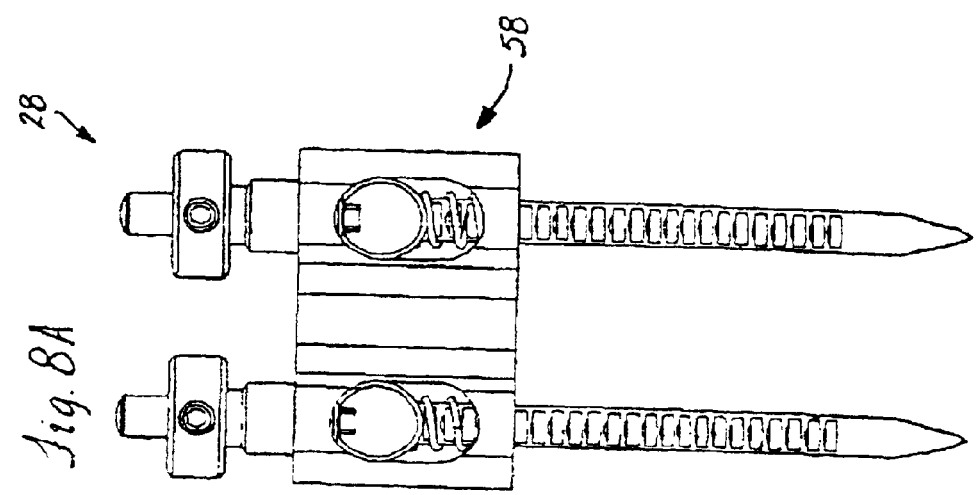

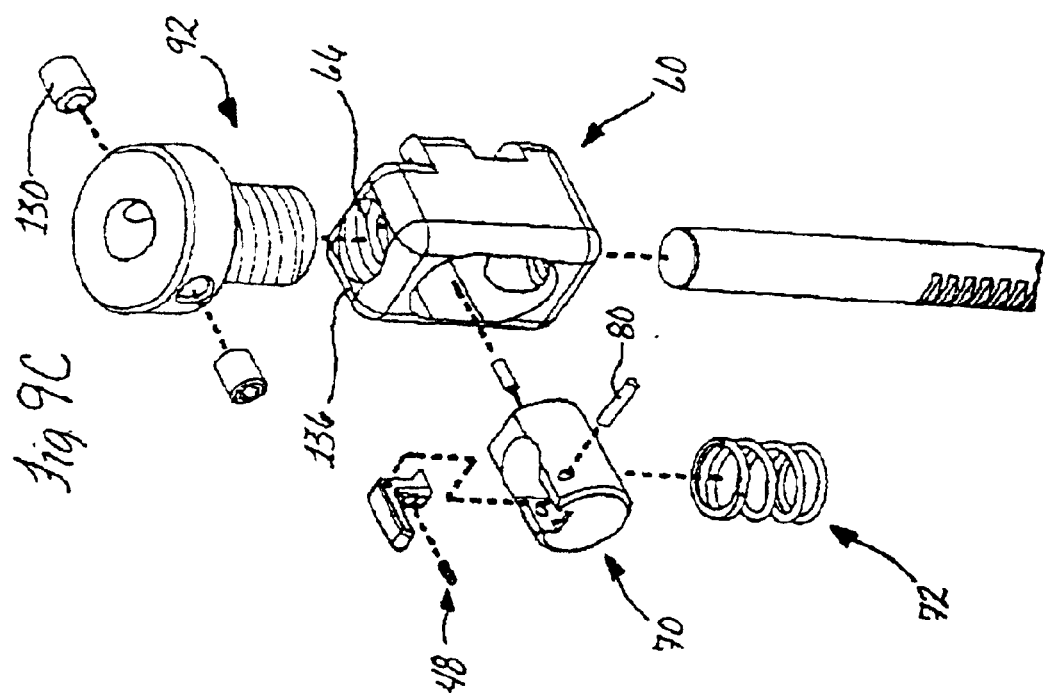
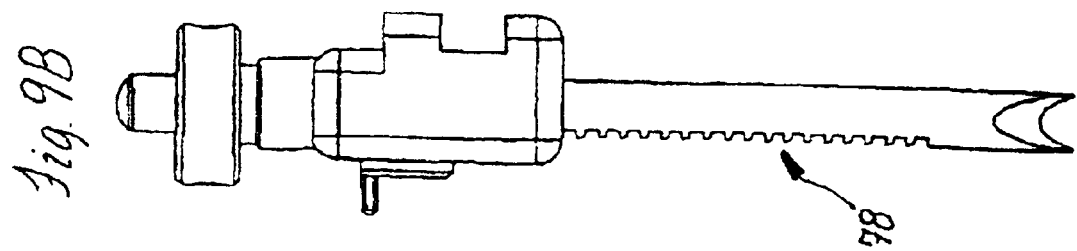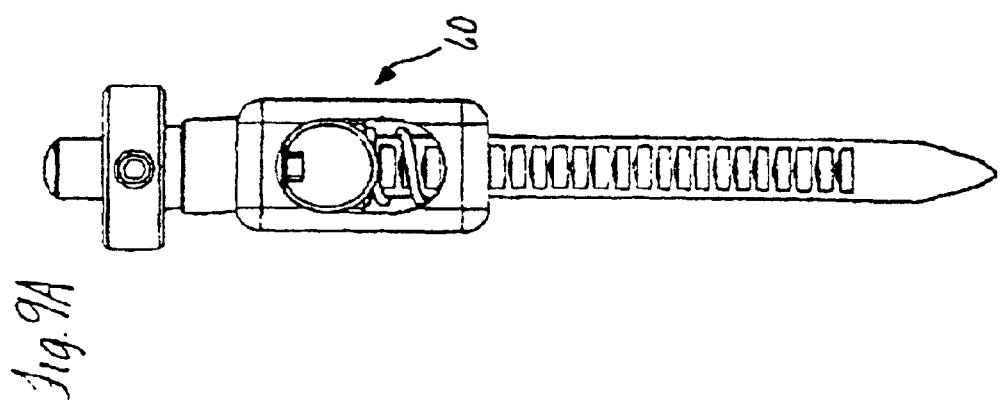

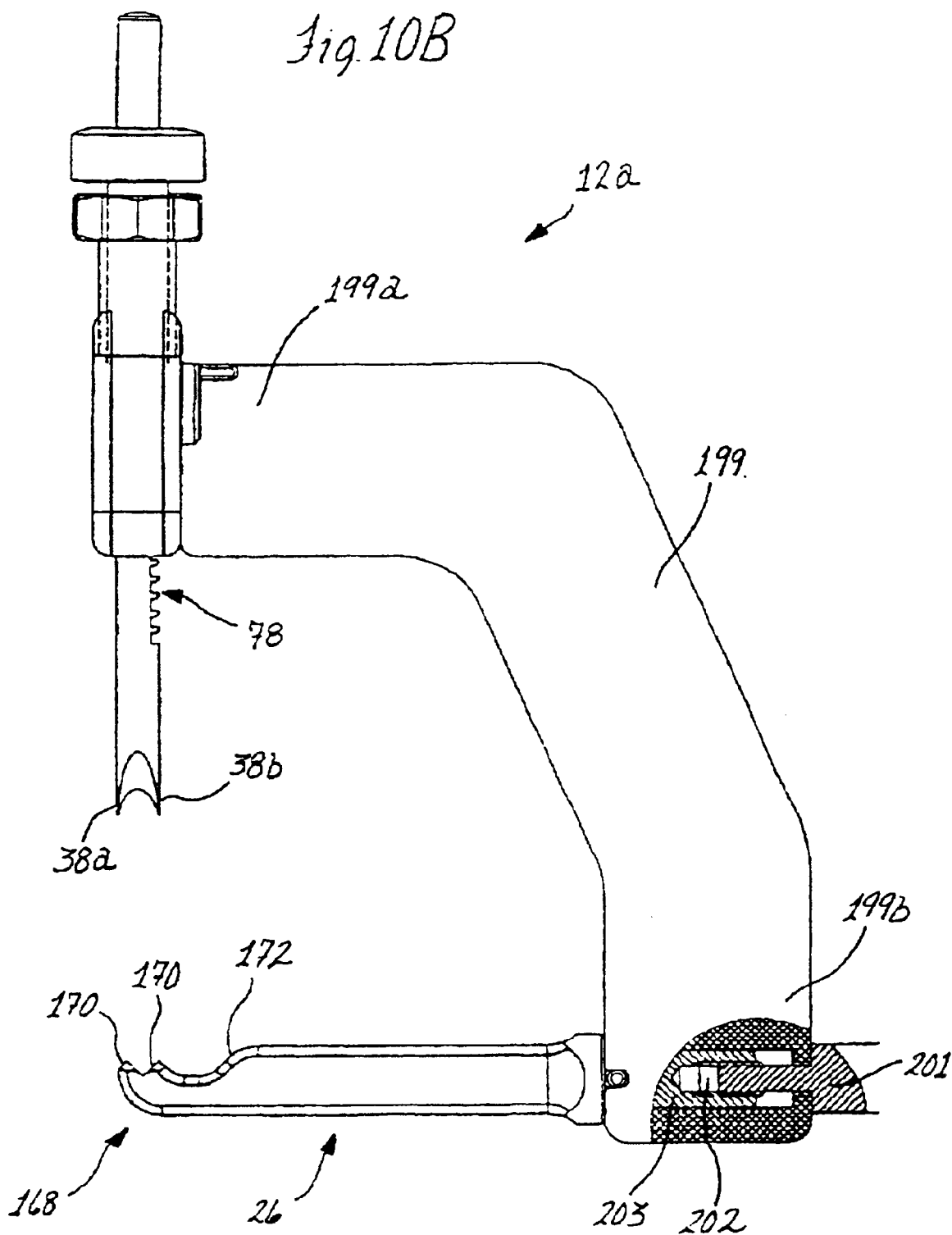

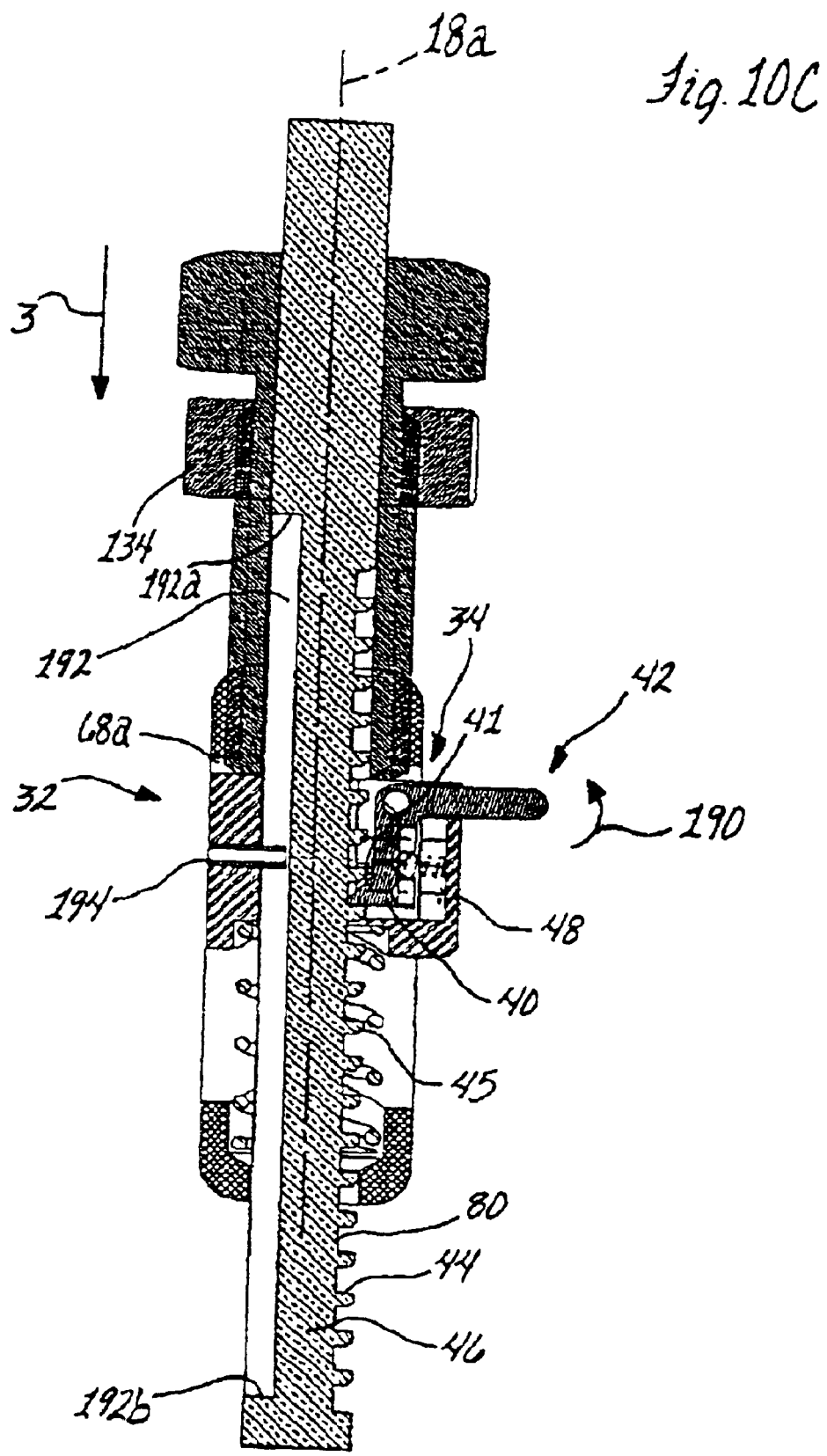

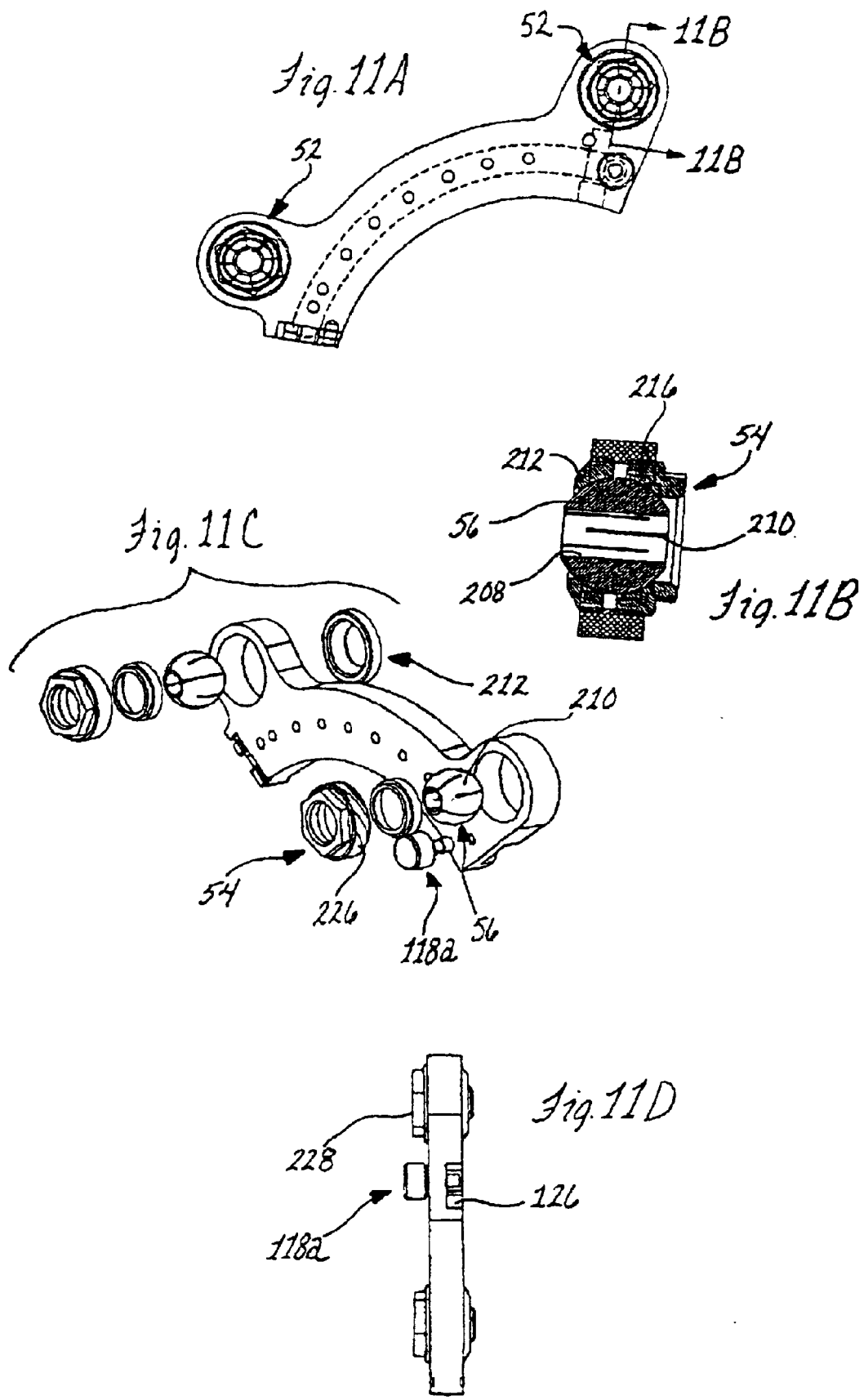

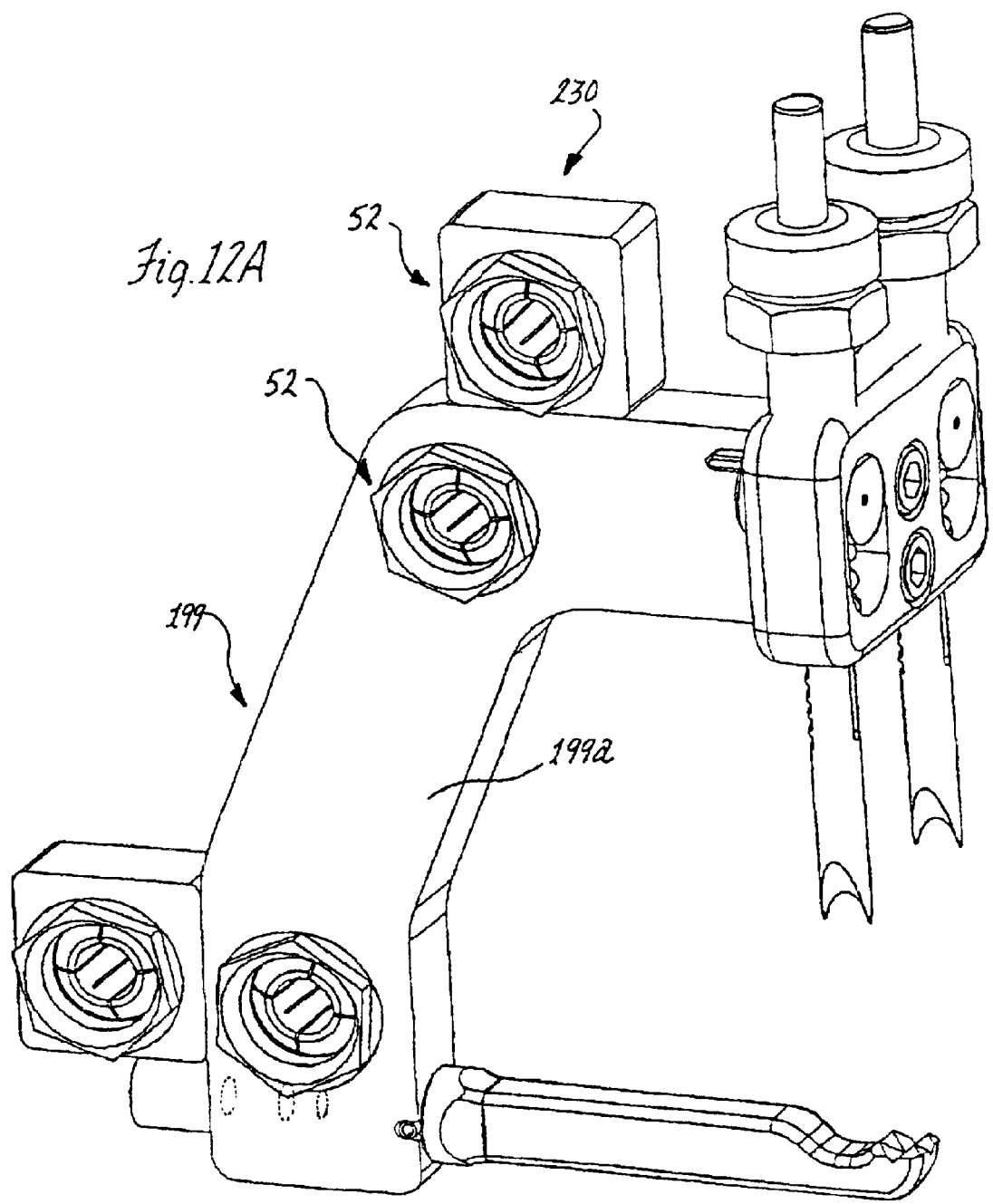

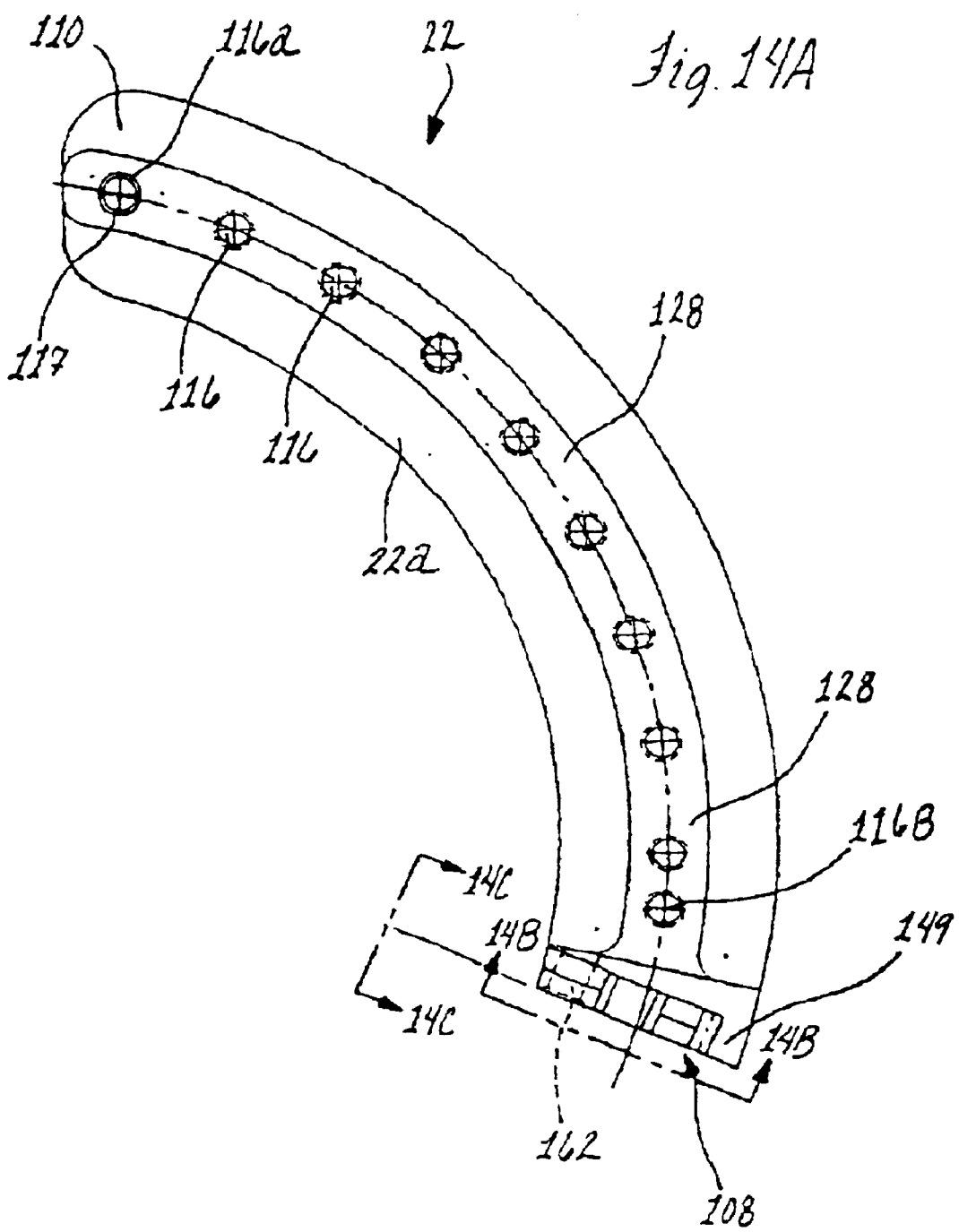

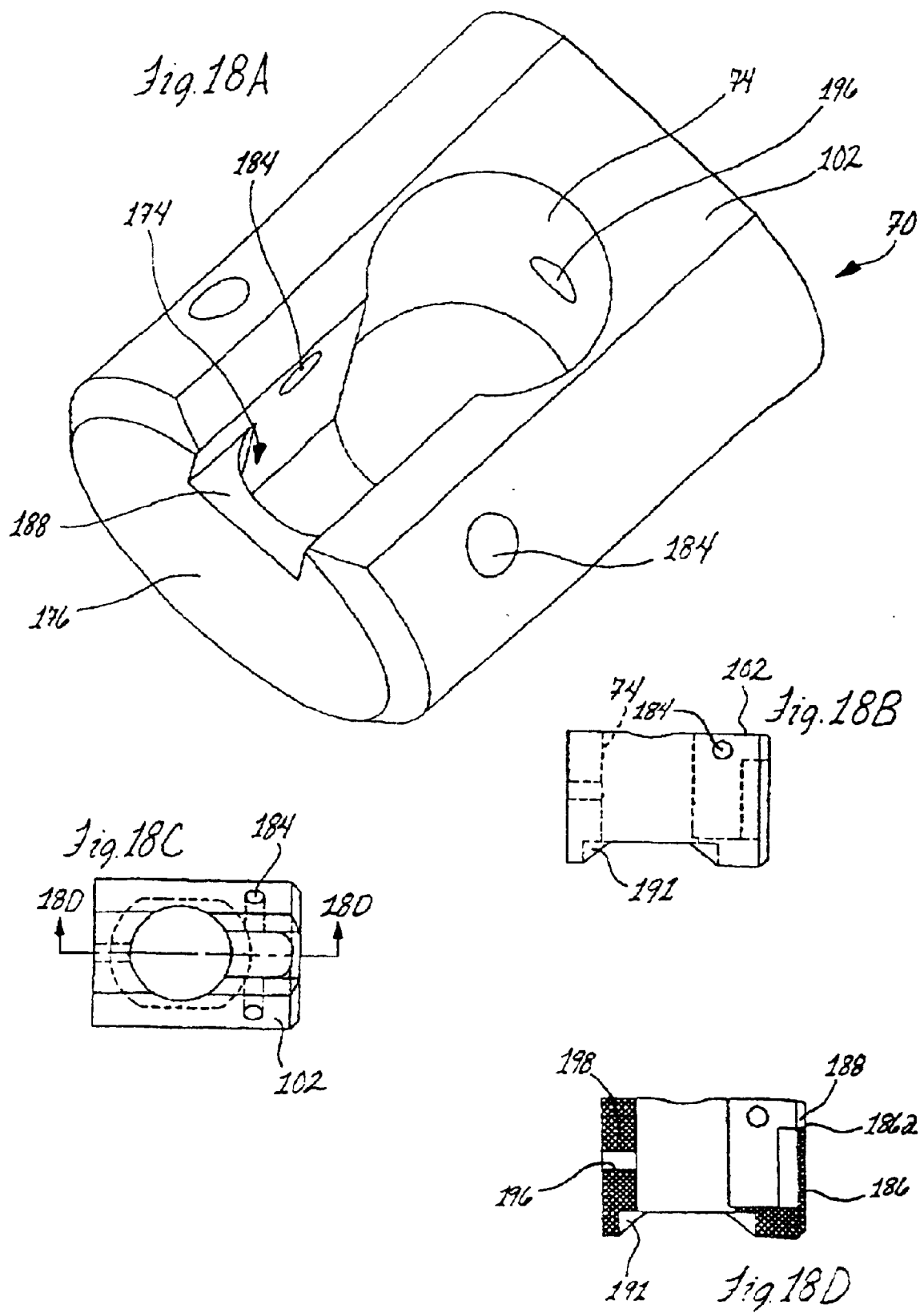

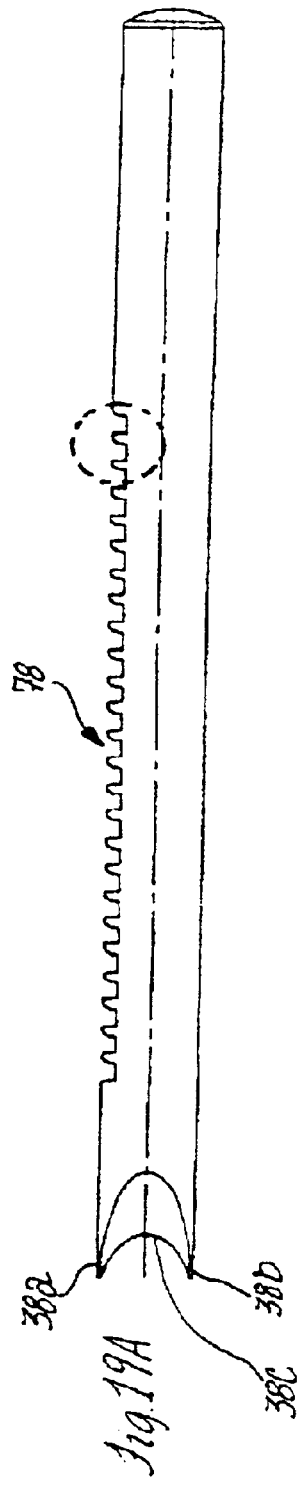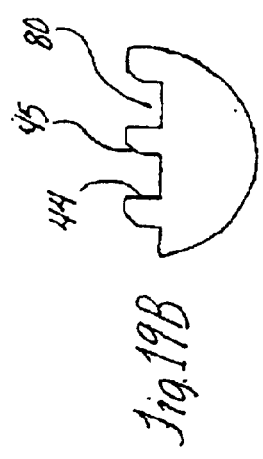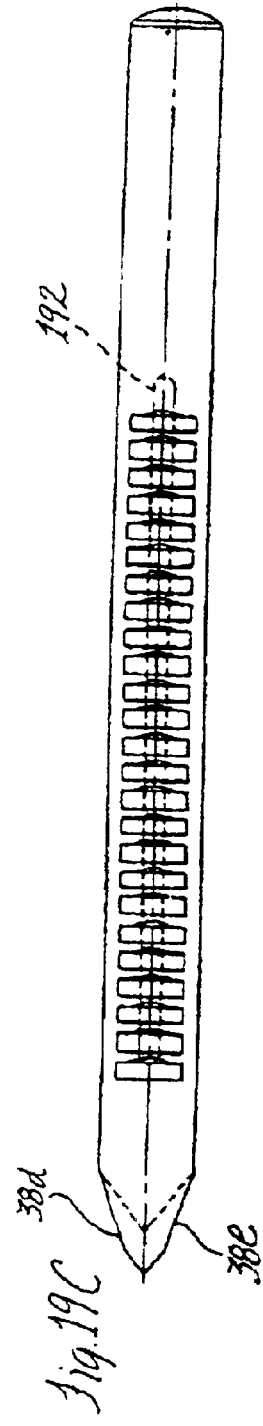

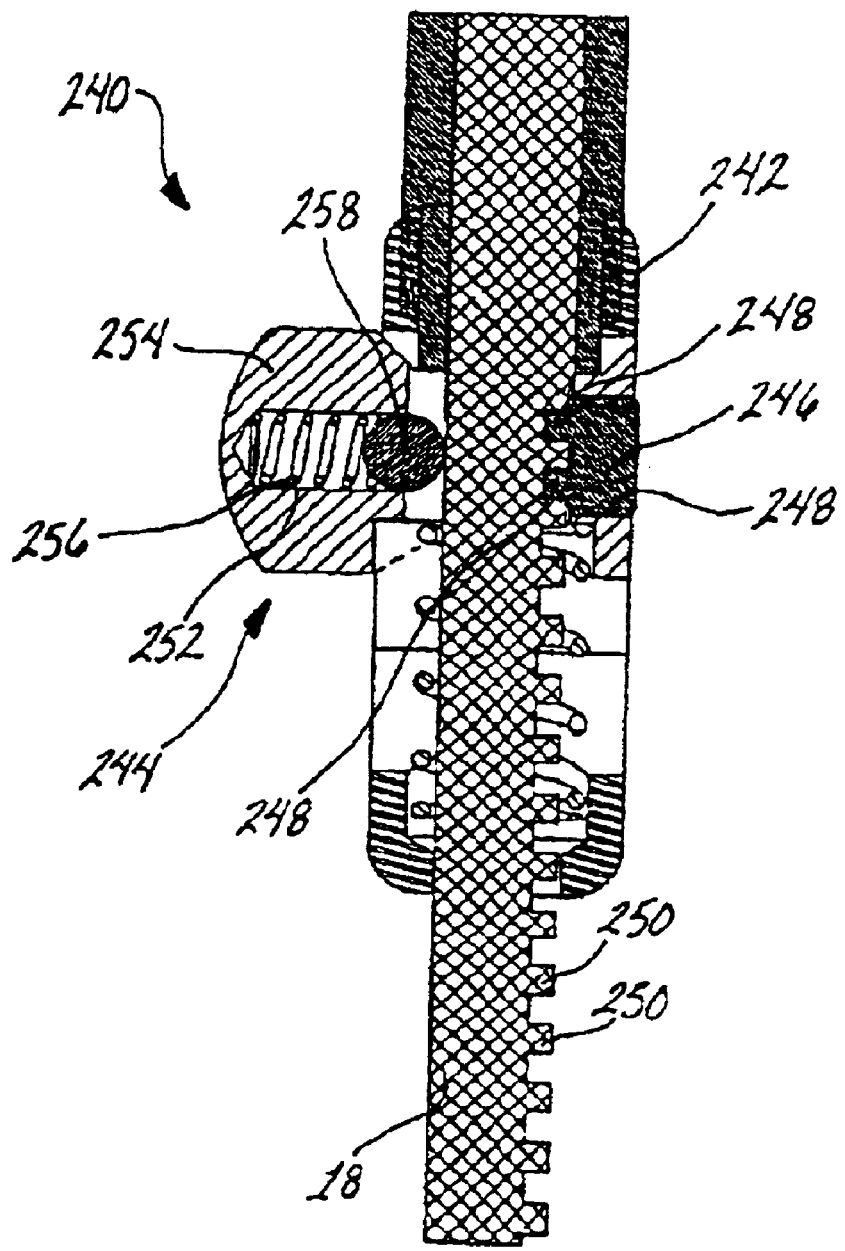

EXTERNAL FIXATION APPARATUS AND METHOD

FIELD OF THE INVENTION

The invention relates to an apparatus and method for fixing bone pins to a bone from external of a patients body and, more specifically, to external bone fixation systems including bone fixators secured along a bone and rigidly connected to each other.

BACKGROUND OF THE INVENTION

It is known to use external bone fixators to reduce fractures in bones such as with fractures of the tibia. Advances in fixators have been made in terms of avoiding the infections that can be caused by use of bone pins that penetrate beyond the bone cortex such as into the tibial canal, or completely through the bone. In these devices, the bone pins typically have a distal bone engaging end having a split prong configuration for tight gripping of the bone surface. Herein, the term non-invasive pins means that the pins do not penetrate the bone canal or the cancellous bone material. Accordingly, when these bone pins are applied in their intended manner they substantially obviate the concern of pin tract infection by use of the fixators.

One problem noted with these generally non-invasive fixation devices is the use of high-force actuators or applicators such as by levers and the like that reduce the user's ability to sense or feel the level of force with which the pins are brought into engagement with the bones and the position at which the pin is engaged with the bone. For example, U.S. Pat. Nos. 6,030,387 and 6,283,965 to Ballier disclose a fixation device that utilizes an applicator gun for driving a displaceable bone pin into engagement with a bone, as by pulling or pivoting the pistol trigger thereof. Pulling the trigger causes a plunger to be driven into engagement with the bone pin for advancing it toward the bone. The applicator pistol can generate forces that are sufficiently high to drive the pin all the way through the tibia. Further, the external arch to which the bone pin is supported is received in a slot at the far end of the barrel of the applicator pistol so that the user's hand generating the application force is somewhat removed from the bone pin and the patient into which it is being applied. This arrangement with the arch cantilevered off the front end of the gun makes it difficult for the user to manipulate the arch into proper position and to control the apparatus during the application process due to the heavy front-loaded weight of the entire apparatus. Further, the user has very little feel or sensory input as to whether there was good anatomical placement of the pin on the bone and the level of force with which the pin was engaged with the bone. As the applicator pistol is not designed to stay with the fixator arch and pins gripped on the bone during healing, further complexities are necessarily added to the Ballier apparatus by the releasable latching mechanism provided between the gun and the arch.

Another shortcoming with fixation devices utilizing non-invasive bone pins involves their stability since the pins are not anchored through the bone. These devices have connecting rods that extend between two such devices having their pins secured onto a bone. In the Ballier devices, for example, the arches have ball receptacles through which the connecting rods are passed and clamped therein after the bone fracture has been reduced for setting the bone in place for healing. The commercial Ballier fixator has these receptacles spaced by approximately 2½ inches and by an angular spacing about a center axis of the bone of approximately 50 degrees. The clamping balls of a Ballier arch are both clamped onto the rods passing therethrough by a single plate. Thus, increasing the separation between the balls entails a corresponding increase in the size of the clamping plate creating extra weight for the apparatus. Extra weight is undesirable from both an application standpoint as earlier considered, as well as from a patient's perspective who will usually have to wear the device for several days during the bone-healing process.

The problem with the small separation of the connecting rods is that the rod connected fixators tend to lack stability as they approach a coplanar relation with the bone axis. In other words, the closer the rods are together, the less stable the whole bone fixation system becomes; similarly, as the angular spacing of the connecting rods approaches 180 degrees, and thus again approximating a coplanar relation with each other, stability in directions transverse to the planes between the rods and bone is lost. With the current Ballier fixators having the above-described small separation and the relatively small angular spacing therebetween, the overall fixation system lacks the rigidity and stability that is desired.

Accordingly, there is a need for an ergonomic and easier-to-use fixation apparatus and method for advancing bone pins into gripping engagement with bone surfaces. An apparatus and method that provides a user with high resolution feel of the engagement forces and placement of the pin on the bone would be desirable. Further, a bone fixation system that has maximum stability as fixed to a bone is needed.

SUMMARY OF THE INVENTION

In accordance with the present invention, a bone fixation apparatus and method are provided that substantially integrates the mechanism for advancing a non-invasive pin to an external pin positioner so as to simplify the apparatus and make the entire apparatus less unwieldily to use. More particularly, the positioner has a pin holder which includes a pin advance assembly integrated therewith. In this manner, the present fixation apparatus avoids the use of an applicator gun or the like so that the positioner is directly gripped by the user for orienting the pins in position for being advanced into engagement with the bone.

The pin holder is preferably formed as a compact housing or module having a through opening which allows the user to manually push the pin at the projecting proximal end thereof in an advancing direction toward the bone for engaging the distal end of the pin therewith. The preferred bone fixation apparatus has a ratcheting mechanism that can operate in the pin holder housing including cam and stop or locking surfaces with the cam surfaces allowing the pin to be ratcheted as the user pushes the pin in the advancing direction and with the stop surfaces automatically engaging, as by a bias force as applied thereto, upon removal of the manual pushing force on the pin so as to keep the pin in the advanced position thereof. To this end, the present bone fixation apparatus allows a user to employ the fingers on the same hand that is gripping the positioner for pushing the pins carried by the pin holders of the positioner in the advancing direction, thus providing one-handed operation of the apparatus herein. Further, the manual pushing of the pin into engagement with the bone allows the user to accurately feel whether the pin is properly engaged with the bone with their finger pushing on the pin.

Another aspect of the present invention relates to controlling the force with which the pin is engaged with the bone. As previously discussed, the pin advance assembly allows the user to manually push a bone pin into engagement with the bone. In the preferred form where a ratcheting-type mechanism is employed, the advanced positions to which the pins can be shifted are in discrete increments defined by interengaging ratchet teeth such as on the bone pin itself and a release member. The release member includes a tooth that is biased into engagement with teeth on the bone pin. An alternative to a ratcheting advance of the pin is simply to use linear sliding thereof with operation of a release member that includes at least one interengaging projection that fits into corresponding projections on the pin. Instead of interengaging projections, the pin can be frictionally held in the pin holder, and the release is operable to create sufficient clearance for sliding of the pin in the advancing direction. The ratcheting mechanism provides for a coarse level of adjustment of the advanced position of the bone pin, and both the ratcheting and the linear advance mechanisms provide a first quick adjust stage to the advanced position of the pin bone-engaging end. In this aspect of the invention, there is a pin advancing mechanism which also includes an adjustment device that allows for fine adjustments to be made to the advanced positions of the pin. In this manner, the pin advancing mechanism employs a two-stage application procedure including an initial quick advance of the bone pin and a final fine-tune adjustment of the engagement forces between the pin and the bone for precision control thereover.

In one preferred form, the pin adjustment device is a screw device which can be threaded to the housing for being turned and advanced into engagement with the preferred ratchet assembly. In this instance, the ratchet assembly is locked to the pin as by the configuration of the teeth thereof, i.e. including stop surfaces, so that engagement of the screw device with the ratchet assembly and advancement thereof causes like advancement of the pin locked thereto. More specifically, the screw device can be threaded to the opening of the pin holder housing through which the bone pin extends as by cannulating the screw member, and the ratchet assembly includes a support block for the release member that is biased into engagement with teeth on the bone pin. As the screw member is turned, it engages the support block of the ratchet assembly for pushing it in the advancing direction.

Other arrangements are also contemplated such as by providing cam threads on the bone pin shaft to allow it to be either linearly advanced as by ratcheting with the shaft threads snapping past the threads on the holder, or the pin can be rotated into engagement with the bone, albeit with the pin including an appropriately configured bone engaging end to accommodate rotation on the bone surface. Similarly, in lieu of direct linear pushing of the pins in their initial stage of quick advance toward the bone, there could be a threaded driver to accomplish the same purpose. The threaded driver can utilize a larger pitch than the fine adjustment screw device so that larger advancing movements are obtained with each turn of the driver. In yet another alternative, a pinion gear can be provided in the pin holder with the gear mating with teeth or threads provided on the bone pin so that turning of the gear shaft causes the bone pin to advance. In each instance, it is preferred that the advancing mechanism be integrated with the holder, and thus stay with the pin positioner during the healing process, and preferably provide for high resolution of the engagement forces between the bone and pin to the user so that they have optimized tactile feedback as to the proper anatomical placement of the pin on the bone and the engagement forces therebetween.

Another form of the present invention relates to enhancing the stiffness of a bone fixation system that employs the non-invasive bone pins herein, i.e. pins which are not intended to penetrate deep into the bone material, such as beyond the bone cortex, and certainly not to be driven all the way through the bone, as in certain prior fixation systems. In the present system, the rigidity and stability of the system having a pair of fixators fixed along a bone is optimized by pins supported thereby advanced into gripping engagement with the bone by the position of rod mounts for the connecting rods extending between the fixators. The positions of the rod mounts are at a predetermined angular spacing so that with the rods received thereby, there is a separation of the rods from a generally coplanar relation with the bone that is substantially optimized to provide stability to the interconnected fixators.

In one form, the angular spacing of the rod mounts about the pin positioner is approximately 80 degrees. While the most preferred angular spacing between the rods would be 90 degrees in terms of system stability, it is clear that the 80 degree spacing contemplated herein is significantly improved over the prior non-invasive Ballier bone fixators which had a relatively unstable spacing of approximately 50 degrees between the connecting rods thereof. To keep the weight of the fixators and the entire system to a minimum, the rod mounts each include flexible receptacles and an independent clamping member for each of the receptacles for clamping on the receptacles and fixing the rods therein. By the provision of independent clamping members for each of the receptacles, the size of the clamping mechanism is significantly reduced as compared to the single large plate that would otherwise be required as employed with the Ballier fixators earlier described. In this way, the clamping rods can have the desired stable separation without requiring an increase in the weight of the fixators.

In another form of the invention, the fixation apparatus includes a pair of pin positioners having arcuately configured bodies. An adjustable connection is provided between the bodies to allow the pins supported thereby to be angularly shifted about a bone for obtaining different angles of pin-to-bone orientation. This provides the bone fixation apparatus with significant flexiblity in terms of where the pins engage the bone so as to allow pin orientations that cause the minimum amount of interference with surrounding nerves, blood vessels, muscles and the like. To this end, it is preferred that pin holders in the form of modules carrying one or multiple bone pins be releasably connected to one of the ends of each of the positioner bodies. With the modular form, a user can interchange the modules on the positioner bodies depending on the number of bone pins needed at the angle of orientation selected for the bone pin or pins for the bone surface to be engaged thereby.

The particular fixation procedure will also inform the selection of the appropriate module therefor. For example, where the fracture is severe and maximum rigidity of the fixators is desired, a surgeon may choose to employ holders each carrying two pins for four point clamping on the bone as opposed to using three-point clamping with a single pin holder and a dual pin holder. By contrast, with smaller bones such as near a joint or where the fixation environment so dictates, two-point clamping can be employed with two single pin modules.

In another aspect of the present invention, a method of fixing bones with bone fixators having bone pins for engaging the bones is provided. The method includes manipulating a pin positioner supporting the bone pins to position the pins for being engaged onto a bone, manually pushing at least one displaceable pin through a pin holder at one end of the positioner to cause the pin to shift in an advancing direction into engagement with the bone at an advanced position thereof, and automatically locking the pin in the advanced position thereof in the pin holder upon release of the manual pushing force applied thereto.

BRIEF DESCRIPTION OF THE DRAWINGS

FIG. 3 is a perspective view of one of the bone fixators showing a pair of adjustably connected pin positioner members with two pins supported at one end of one of the members and one pin supported at one end of the other member and the members adjusted to a 180 degree separation of their respective pins;

FIG. 5 is a perspective view of one of the positioner members having two pins supported at one end and a single fixed pin supported at its other end with a 90 degree separation between the pins;

FIG. 8A is a front elevational view of a pin holder module carrying two bone pins for being advanced into engagement with a bone;

FIG. 8B is a side elevational view a pin holder module of FIG. 8A showing a proximal end of the pin projecting from the module, a distal end of the pin configured for gripping engagement with the bone, and a plurality of teeth formed along the pin;

FIG. 8C is an exploded perspective view of the pin holder module of FIGS. 8A and 8B showing a screw member for making fine adjustments to the position of the bone pins, and a support block and release lever of the pin advance assembly for being operably connected to the pin;

FIGS. 9A–9C are similar to corresponding views of FIGS. 8A–8C except showing a pin holder module carrying a single bone pin;

FIG. 10B is a side elevational view of the bone fixator of FIG. 10A showing the configuration of the distal bone engaging end of the fixed bone pin including a raised abutment for indicating engagement with the bone;

FIG. 10C is a cross-sectional view taken along line 10C—10C of FIG. 10A showing the release lever biased into engagement with the bone pin teeth and the support block biased to the top of a fine adjust travel limiting slot in the housing module;

FIG. 11A is a side elevational view of one of the positioner members including an arcuate body having a female groove including a series of apertures for the adjustable connection with the other positioner member;

FIG. 11B is a cross-sectional view taken along line 11B—11B of FIG. 11A showing a flexible ball rod mount assembly for receipt of a connecting rod therethrough;

FIG. 11C is an exploded view of the female positioner member body showing a clamping ball holder and ring between which a resilient ball is held and a clamping nut that clamps the ball onto the connecting rod;

FIG. 11D is an end elevational view of the assembled female positioner member showing a fastener for being connected to the other positioner member;

FIG. 12A is a perspective view of a bone fixator similar to that shown in FIGS. 10A–10C including additional rod mounts attached to the positioner member body thereof;

FIG. 14A is a side elevational view of the male positioner body showing a central-raised rib for mating in the groove of the female body and having a series of adjustment apertures formed therein;

FIG. 18A is a perspective view of a support block for pivotally mounting a release lever therein with the block received in the pin housing module and projecting in the travel limiting slot thereof;

FIG. 18B is a side elevational view of the support block of FIG. 18A showing a passageway extending therethrough and through which the bone pin extends and opening to a wider lower portion for receipt of end coils of a compression spring;

FIG. 18C is a plan view of the support block showing the through opening and transversely oriented apertures for receipt of a pivot pin for the release lever;

FIG. 18D is a cross-sectional view taken along line 18D—18D of FIG. 18C showing an upstanding wall of the block spaced from the through passage for receipt of a spring between the wall and the lever;

FIG. 19A is a side elevational view of one of the bone pins showing a shaft having the plurality of cam teeth formed therealong;

FIG. 19B is an enlarged view of three of the teeth of the bone pin;

FIG. 19C is a front elevational view of the bone pin showing an elongate slot in phantom diametrically opposed to the teeth about the shaft;

FIG. 23 is a cross-sectional view of an alternative pin advance assembly showing a button release member and interengaging projections biased into engagement with a rack of projections formed along the pin shaft.

DETAILED DESCRIPTION OF THE PREFERRED EMBODIMENTS

Figure 1:
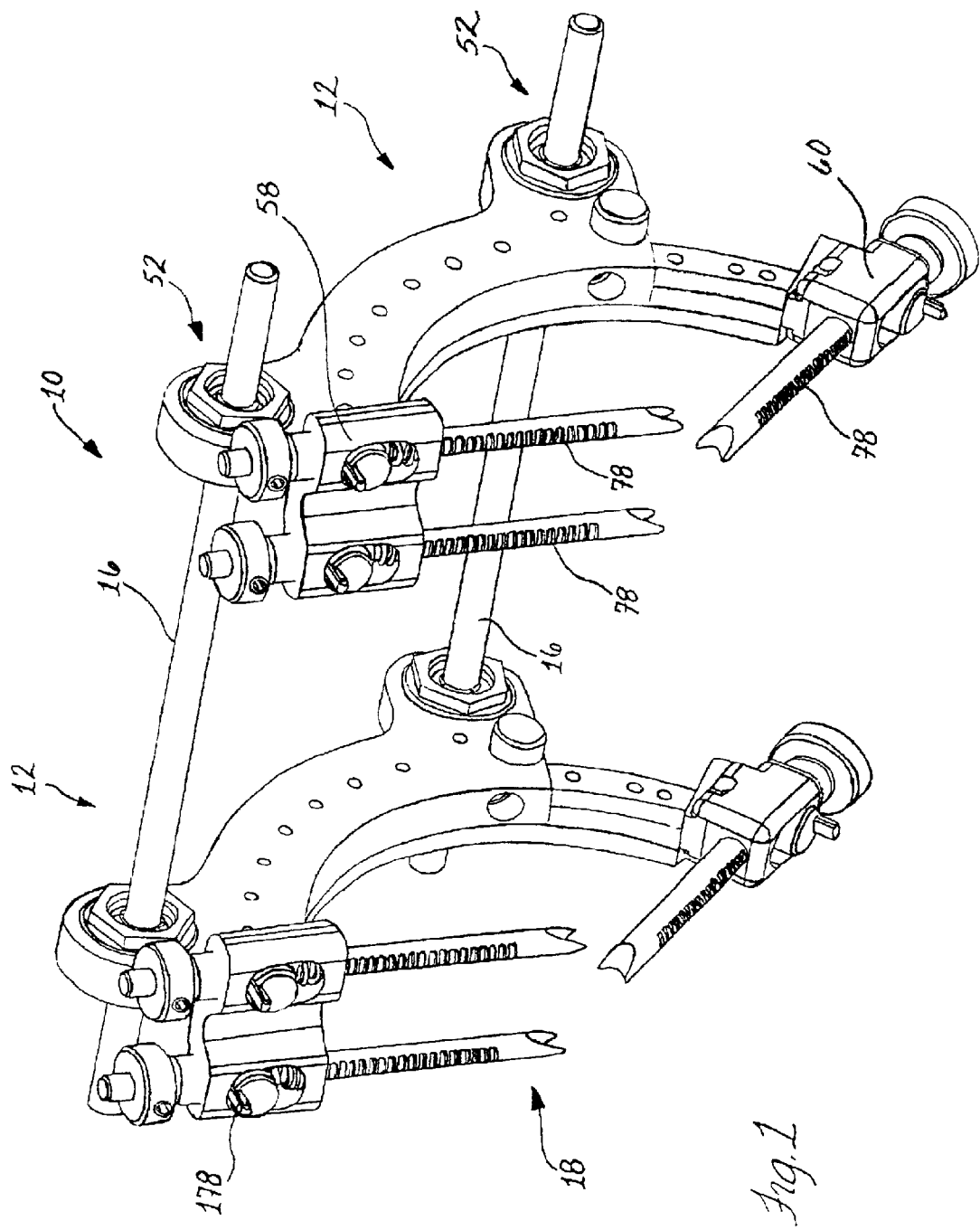
FIGS. 1 and 2 are front and rear perspective views, respectively, of a bone fixation system in accordance with the present invention showing a pair of bone fixators interconnected by a pair of connecting rods.
Figure 2:
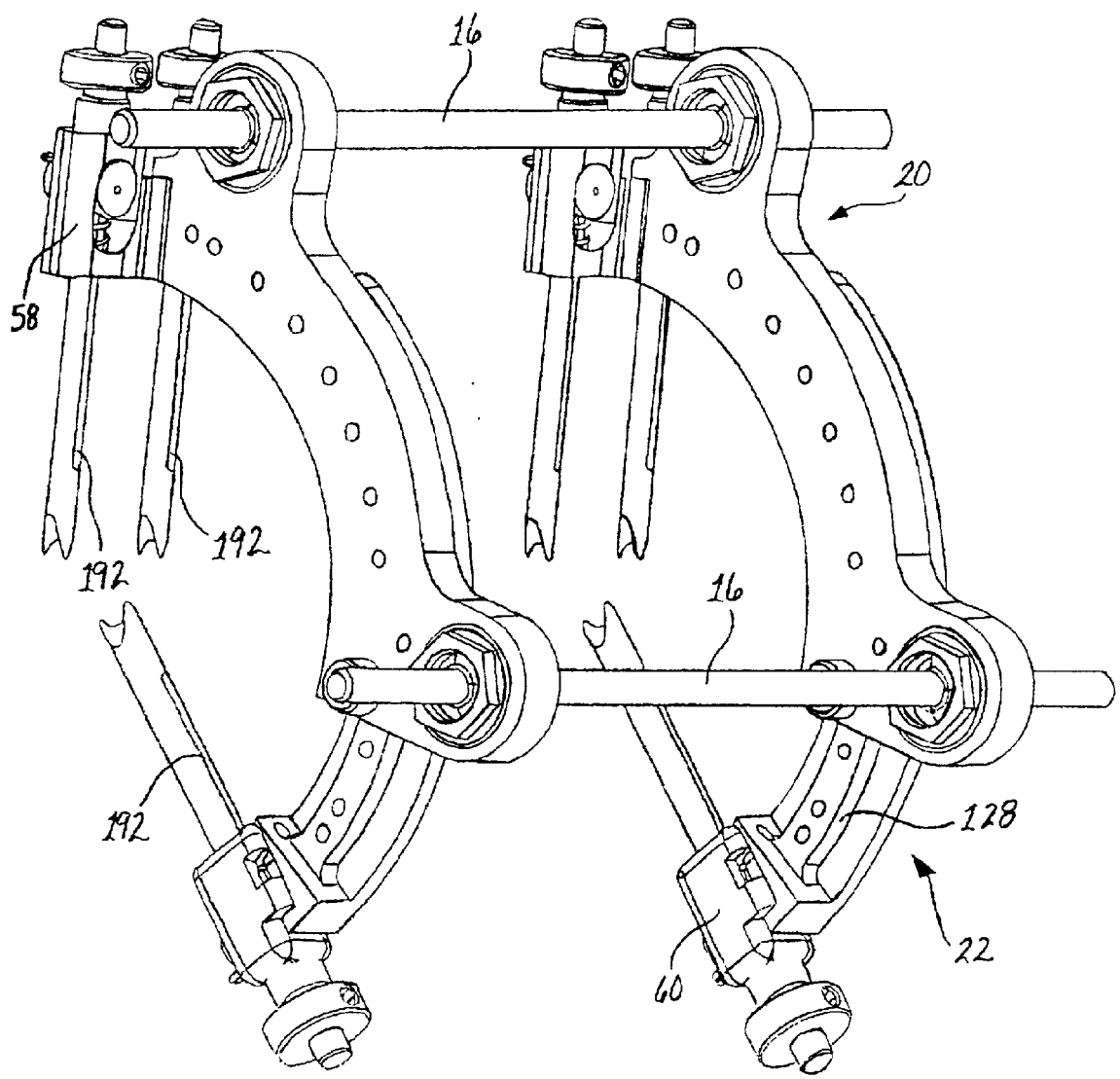

In FIGS. 1 and 2, a bone fixation system generally designated 10 is depicted in its preferred form having bone fixators 12 for being pinned to a bone such as the tibia 14 with the fixators 12 interconnected by rods 16. The present system 10 including the fixators 12 is improved in several respects over prior external bone fixation systems. These improvements relate to the ease with which the bone pins 18 are applied to the bone 14 and the ability of the user to accurately sense proper anatomical placement of the pins 18 on the bone 14 and the level of force with which the pins 18 are engaged therewith.

Further improvements relate to other ergonomic aspects such as the size of the fixators 12 which keeps the user applying the pins 18 close to the application site again making proper application of the pins 18 easier and making the device more comfortable to wear over sustained periods of several days, as will commonly be the case with tibia fractures and the like. To this end, the present system 10 also improves on the stability of the connected fixators 12 by optimized positioning of the connector rods 16. Other improvements also relate to the flexiblity of the fixators 12 in terms of the orientation of the pins 18 relative to the bone 14 to be pinned as well as the type and number of the pins to be utilized. In each instance, these improvements can be incorporated in bone fixators generally independent from one another, although in its most preferred form, the system 10 and the fixators 12 herein are adapted to implement each of the above-discussed enhancements to maximize use of the present system 10 by doctors or other medical personnel (herein termed "users").

Figure 4A:
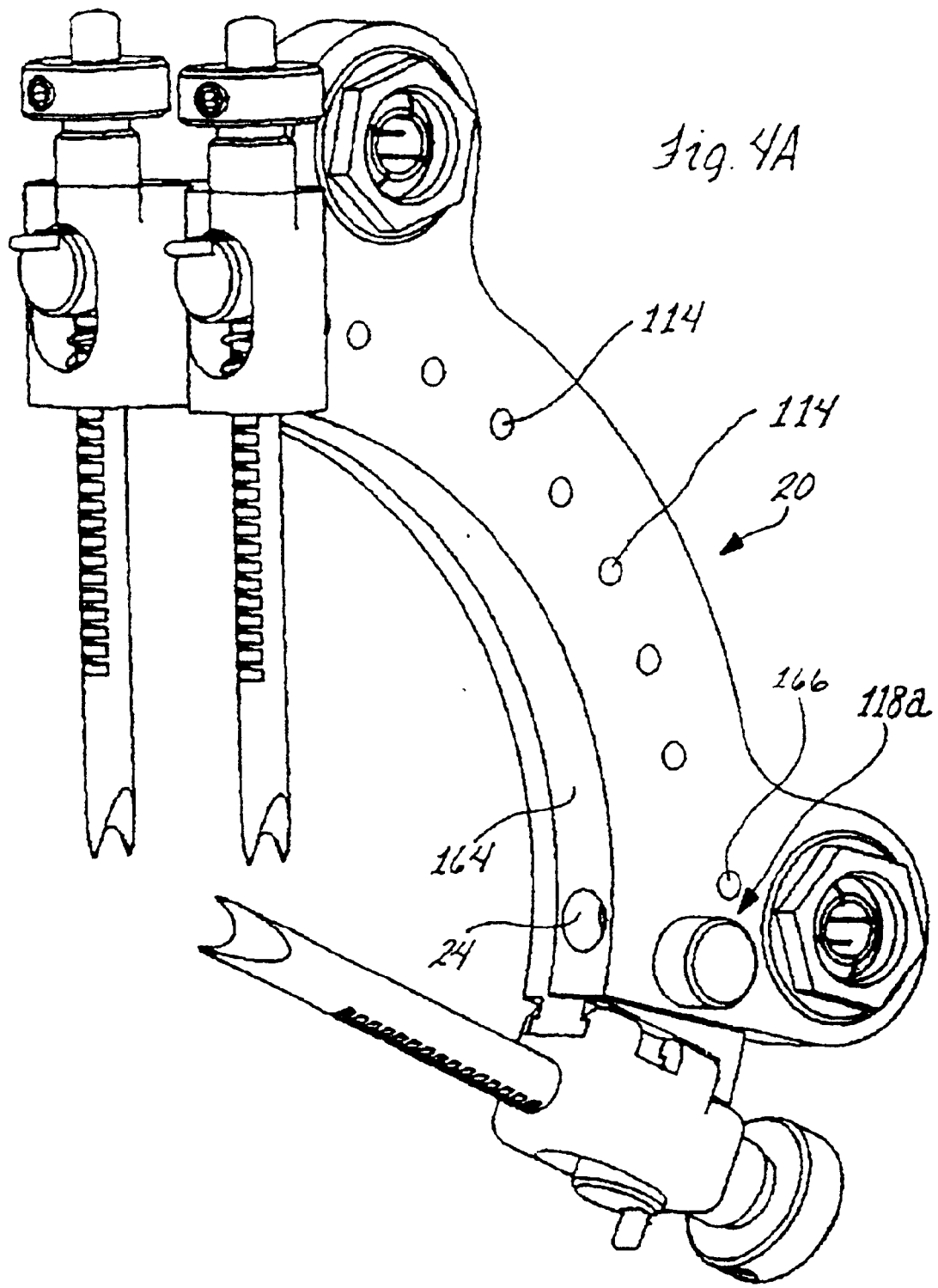
FIG. 4A is a view of the bone fixator showing the positioner members adjusted to a 115 degree angular separation of the pins supported at the ends thereof.

The bone fixators 10 each include a pin positioner which preferably include two positioner members 20 and 22, although as will be described hereinafter a single positioner member can also be utilized. As best seen in FIGS. 3 and 4A, the positioner members 20 and 22 are adjustably secured to each other to provide a range of relative positions between bone pins 18 supported thereby. This allows a user to orient the pins 18 as needed such as depending on the configuration of the surfaces of the bone 14 to be fixated. As shown, the positioner members 20 and 22 allow their respective pins 18 to be oriented at angular spacings between approximately one-hundred and eighty degrees (FIG. 3) and one-hundred and fifteen degrees (FIG. 4A) with respect to each other. The positioner members 20 and 22 can also be detached from each other, and the positioner member 20 includes a pin receiving aperture 24 in which a fixed bone pin 26 (FIG. 5) is held at a generally ninety degree angular spacing from the other pins 18 supported thereby.

The positioner members 20 and 22 support their respective bone pins 18 via pin holders 28 and 30 that each incorporate a pin advance assembly or mechanism 32 therein, such as can be seen in FIG. 10C. The pin advance assembly 32 preferably includes a ratchet mechanism 34 as by cam surfaces between the holders 28 and 30 and the pins 18 which allows the user to shift the pin 18 in an advancing direction as indicated by arrow 33 toward the bone 14 as by a manual push force applied to proximal ends 36 of the pins 18 to bring the bone engaging distal ends 38 into engagement with the bone 14. The ratchet mechanism 34 includes a locking mechanism formed by stop or lock surfaces disposed between the pin holders 28 and 30 and the bone pins 18 extending therethrough, such as surface 40 on release member 42 and surfaces 44 on shaft 46 of the pin 18 which automatically are brought into abutting engagement with each other upon release of the manual force from the pin end 36, as by a predetermined bias force provided by spring 48 acting between the release member 42 and housing 50 of the holders 28 and 30. In this manner, once the user stops pushing on the pin 18, its advanced position is securely locked in place by the cooperating abutting stop surfaces 40 and 44 so that the pin 18 cannot back or retract away from the bone 14. Similarly, the cam surfaces can be disposed on release member 42 including cam surface 41 and on the pin shaft 46 including a plurality of cam surfaces 45.

As previously mentioned, the angular spacing and separation of the connecting rods 16 is optimized from a stability standpoint via the corresponding spacing of rod mounts, generally designated 52, provided on one of the positioner members 20 or 22. As shown herein, the rod mounts 52 are attached to the positioner member 20. In prior non-invasive fixators, the spacing between the connecting rods 16, which can be of various elongate configurations such as solid or cylindrical, was not optimized as corresponding rod mounts 52 were constrained in their separation by the size of the single clamping plate used to secure the rods in place as previously described. The present rod mounts 52 employ independent clamping members in the form of clamping nuts 54 that can clamp onto resilient or flexible clamping balls 56 in which the connecting rods 16 are received, the components of the assembly of the rod mounts 52 being shown in FIG. 11C.

As is apparent, these clamping nuts 54 are relatively small in size and do not add significant weight to the fixators 12 herein. By use of independent clamping members 54, the separation of the rod mounts 52 can be optimized. In this regard, the optimum spacing of the pair rods 16 is their maximum spacing from a coplanar relation with such plane defined through the bone pinned with the fixators 12 herein, i.e. at approximately 90 degrees angularly spaced from each other. In the illustrated fixators 12, the rod mounts 52 and thus the connecting rods 16 attached thereto are angularly spaced at approximately 88 degrees from each other with a separation of approximately 5½ inches. When secured to a bone 14, it is anticipated that the angle formed between the rod mounts 52 and rods 16 secured therein such as measured from the bone axis 14a will be approximately 80 degrees. This is a significant improvement over prior devices utilizing a single clamping plate for clamping on their corresponding resilient clamping balls which in practice angularly space the rods by approximately 50 degrees and have a 2½ inch separation, as previously mentioned. Accordingly, the present fixators 12 when interconnected by the rods 16 will be highly rigid as forces transverse to the planes between the rods 16 and the bone 14 will tend to be stabilized by the optimized spaced positions of the rods 16 and the maximized separation therebetween. In other words, the bone 14 and rods 16 which are all fixed to each other will provide an optimally spaced three-point mounting of the fixation system 10 herein including at least two interconnected fixators 12 such as at corners of an approximately right triangle arrangement with the hypotenuse maximized in length, i.e. the linear distance between the rods.

Returning to a description of the pin holders 28 and 30 and the ratchet mechanism 34 integrated therein, the pin holders 28 and 30 primarily only differ with respect to the number of pins 18 they carry, and thus only dual pin holder 28 will be described in great detail herein. As shown in FIGS. 8A–8C, the pin holder 28 carries two pins 18, while the pin holder 30 shown in FIGS. 9A–9C carries only a single pin 18, which can be of slightly greater diameter than the two pins 18 carried by the dual pin holder 28 to provide it with greater resistance to bending. The pin holders 28 and 30 are preferably formed as modules each having a housing 58 and 60, respectively, that can be releasably attached to an end of each of the positioner members 20 and 22 to provide the user flexibility in terms of the type and number of pins 18 to be employed for gripping the bone. As can be seen, the main difference between the holders 28 and 30 is in the construction of the housings 58 and 60 with the dual pin housing 58 having a pair of parallel throughbores 62 and 64 formed therein, whereas the single pin housing 60 has a single throughbore 66 with the throughbores 62–66 configured for receiving the shafts 46 of the pins 18 therethrough.

Each of the housings 58 and 60 has a very compact configuration. For example, the larger dual pin housing 58 can have a 2.00 inch width and a height of 1.20 inches with a depth or thickness of the housing being approximately 0.75 inch. As is apparent, the compact configuration of the housings 58 and 60 herein having the pin advance mechanism or assembly 32 integrated therein enables them to be mounted to the positioner members 20 and 22 without causing a significant increase in size of the fixators 12 herein. In this manner, the holder modules 28 and 30 are well adapted for staying with the fixator 12 without removal therefrom after their pins 18 have been secured onto the bone 14, such as required with prior pistol applicators as previously described. Further, the compact nature of the modules 28 and 30 enables the user to be very close to the incision through which the pins 18 are to be pushed or driven into engagement with the underlying bone 14 to improve accuracy and control over their application. Also, the fixators 12 herein contemplate that the user can be gripping the positioner with one hand to orient the pins 18 in the desired angle of orientation relative to the bone 14 while allowing fingers on the same hand that is holding the positioner to be utilized for advancing the pin 18 into engagement with the bone 14, thus allowing for one-handed operation of the present fixators 12.

The following is a description of the components of the pin holder modules 28 and 30 including the pin advance assemblies 32 thereof with reference to the module 28 specifically, with the corresponding components between the modules 28 and 30 being designated by the same reference numbers. The housing 58 has a pair of identical transverse through slots 68 that each intersect with respective axial through bores 62 and 64 with the housing 60 including a single slot 68 that intersects its throughbore 66. Extending through each slot 68 is a support block or slot follower 70 that is urged toward the proximate end 68a of the slot 68 via a bias force provided by spring 72. Each support block 70 can have a generally cylindrical outer configuration and include an axial through opening 74 aligned with the respective throughbores 62 and 64 of the housing 58 for receipt of the pin shafts 46 therethrough. To this end, the block spring is preferably a coil spring 72 with coils of sufficient diameter to allow the pin shaft 46 to fit therethrough. The support block 70 supports the release member which in the preferred form is a release lever 42 having a tooth end 76 that is biased into engagement with ratchet teeth 78 formed along the pin shaft 46.

The stop surface 40 and the cam surface 41 are formed as lower and upper surfaces on the lever tooth end 76, and the stop surfaces and cam surfaces, 41 and 45, on the pin shaft 46 are formed as upper and lower surfaces of the teeth 78, respectively. More specifically and referencing FIG. 10C, it can be seen that the lever 42 is biased so that the tooth 76 thereof securely engages in the rack of teeth 78 on one side of the pin shaft 46 with the respective upper and lower cam surfaces 41 and 45 of the lever tooth 76 and pin teeth 78 in facing relation, and the respective lower and upper stop surfaces 40 and 44 of the lever 42 and the pin teeth 78 in facing relation. Alternatively, the cam surfaces can be provided on either of the lever end 42 or pin teeth 78 to provide the requisite camming action.

For one-way ratcheting of the bone pin 18 in the advancing direction 33, the cam surfaces 41 and 45 are similarly inclined to axis 18a of the bone pin while the stop surfaces 40 and 44 extend normal thereto. Accordingly, when a user pushes downwardly on the proximal end 36 of the pin 18, the surfaces 41 and 43 engage and cam against one another with the downward force causing the lever 42 to pivot about pivot pin 79 mounted in the block 70 against the bias force provided by spring 48 until the ends of the surfaces 41 and 45 clear each other, whereupon the spring 48 causes the lever tooth end 76 to click back into one of the spaces 80 formed between adjacent pin teeth 78. In this manner, the stop surfaces 40 and 44 are automatically brought back into confronting relation preventing the pin 18 from backing away from the advance position to which it has been incrementally ratcheted by the pushing force applied by the user at the pin proximal end 36. Thus, any attempt to pull the pin 18 away from its advanced position will cause the stop surfaces 40 and 44 to engage, stopping any travel of the pin 18 in the retracting direction, and essentially locking the pin 18 in place in the advanced position thereof.

One advantage of the preferred pin advance assembly 32, such as employing the one-way ratchet mechanism 34, where the user has to push directly on the pin proximal end 36 for shifting the pins 18 in the advancing direction 33 thereof is that the user will be able to better feel whether the distal pin end 38 is properly engaged on the bone 14. In prior systems where the bone pin 18 is not directly engaged and/or is driven by several intermediate force-applying members such as a pistol trigger and a plunger in the Ballier devices, there can be a significant amount of force dissipation from the pin end 38 to the users fingers so that the user can not accurately gauge the force with which the pin 18 is engaging the bone 14. With the preferred pin advance assembly 32, there is very little force dissipation between the distal end 38 of the pin and the proximal end 36 of the pin at which the user's finger is engaged. Accordingly, the present fixator apparatus 12 provides the user with high level resolution of the engagement forces between the pin end 38 and the bone 14 so that they can readily feel whether the pin end 38 is securely engaged on the bone 14 and with how much force this engagement is occurring.

Figure 7:
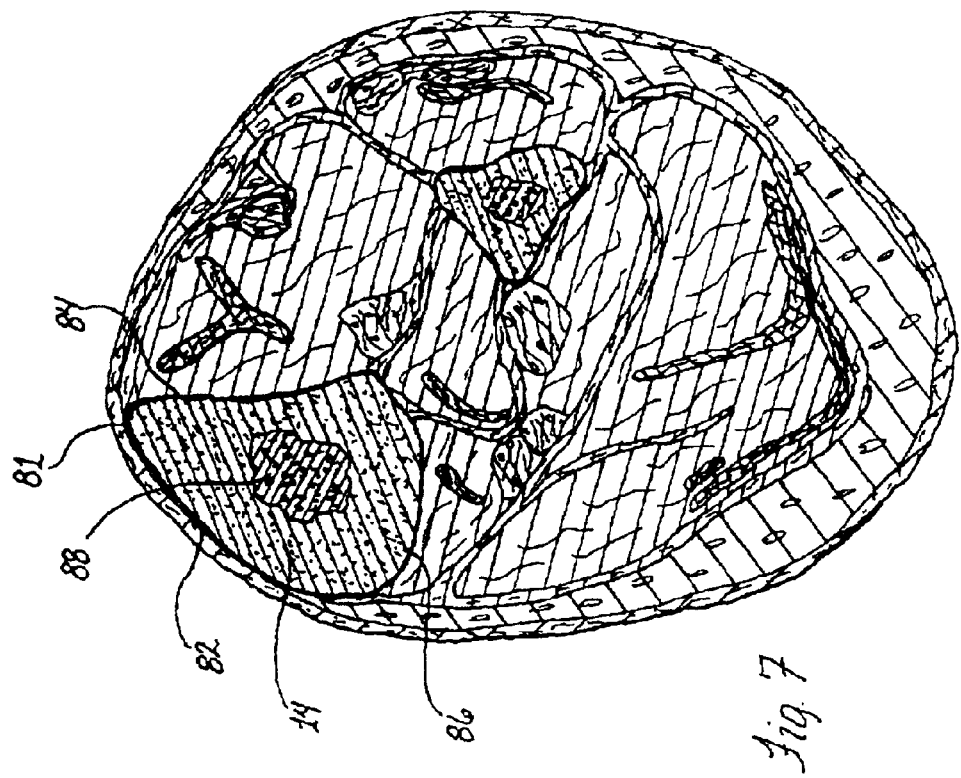
FIG. 7 is an enlarged cross-sectional view through the lower leg to show the cross-sectional configuration of the tibia.
Figure 6:
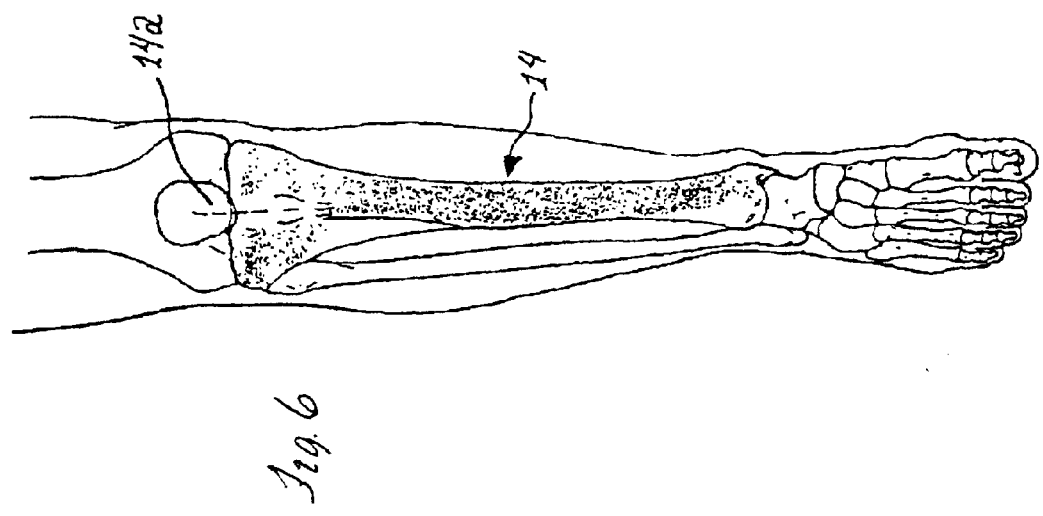
FIG. 6 is a front elevational view of leg bones in the lower portion of a leg including the tibia to which the present bone fixation system herein is commonly affixed.

The enhanced tactile feedback provided by the present fixators 12 is very important as bones 14 to be secured with the present fixation system 10 can vary widely in configuration from one bone to the next as well as along the length of a single bone with very complex, contoured surfaces. Further, the location of the bone 14 in the human body can introduce complications in terms of the surrounding viscera making it difficult to access certain bone surfaces. For example, and referencing FIGS. 6 and 7 with respect to the lower leg, it can be seen that the tibia 14 varies in size as well as shape along its length as it extends between the knee and foot. As can be seen in FIG. 7, the cross-sectional configuration of the tibia bone 14 has a generally triangular shape with an anterior ridge 81 at the front of the leg having surfaces 82 and 84 tapering away therefrom, and posterior surface 86 extending therebetween.

As is apparent, the previously-described ratchet mechanisms 34 for each of the bone pins 18 carried in holder 58 are independently operably from each other so as to allow them to be extended to different advanced positions. This functionality is especially useful where the pins 18 are to be engaged on contoured bone surfaces that vary in depth from the dual pin holder 58 to avoid the situation where the pins 18 if fixed at the same advanced position would only allow one of the pin ends 38 to securely clamp onto the contoured bone surface.

Generally, the most desired location for engagement of the pins 18 is at the anterior ridge 81 and the anterior surface 82 close to the skin since the surfaces 84 and 86 are surrounded with nerves, blood vessels, muscles and the like. However, when the surfaces 84 and 86 need to be accessed for application of bone pins 18 thereto, the ability of the user to feel the bone pins 18 progression through the leg and into engagement with one of the surfaces 84 and 86 is of particular value since the surfaces 84 and 86 typically cannot be readily viewed through the incision. Moreover, even with the anterior ridge 80 and the surface 82, the ability of the user to have a precise tactile feel of when the pin 18 is engaging the bone 14 provides great assistance in allowing them to determine whether the pin 18 is properly engaged thereon and to be able to limit the penetration depth of the distal tip end 38 and prongs 38a and 38b thereat into the outer hard cortex material of the bone 14 so that they penetrate far enough for secure gripping on the bone 14 but do not extend so far as to project into the tibial canal 88.

A further advantage of the illustrated arrangement of the bone pins 18 is that the dual pins 18 are arranged to engage on the tibia anterior ridge 81 with the single pin 18 arranged to engage one of the other surfaces 82–86. Where the single pin 18 is to engage tibia surface 84 and 86 it reduces the possibility for damage to the surrounding tissue, muscle, etc. as opposed to the split-dual pin configuration used for engaging these surfaces in the Ballier devices.

The illustrated bone pin 18 has the tip ends or prongs 38a and 38b separated by an arcuate or concave sharp edge 38c therebetween, as best seen in FIG. 19A. In addition, opposite faces 38d and 38e are contoured and taper toward each other to the arcuate edge 38c. The concave edge 38c substantially sets the depth of penetration of the prongs 38a and 38b to ensure that they are not advanced too far into the bone material, e.g. into cancellous material. A wide variety of configurations for the bone engaging pin end 38 could be employed such as a pin end having a single central extended point with a sharp annular edge recessed back from the pin end which would allow the bone pin to be rotated for fine tuning the clamping forces as with a bone pin configured with cam threads, as has been mentioned previously.

Figure 17A:
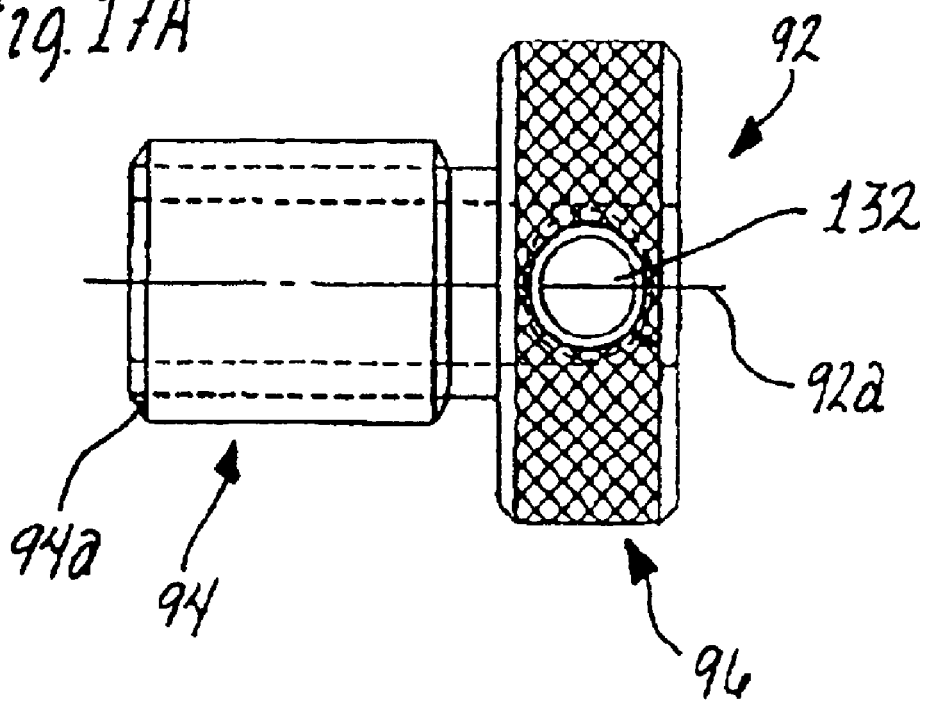
FIG. 17A is a side elevational view of a cannulated screw member for being threaded to the through openings of the pin holder module housing showing a transverse threaded aperture in an enlarged head thereof for receipt of a set screw to lock the pin in position.
Figure 17B:
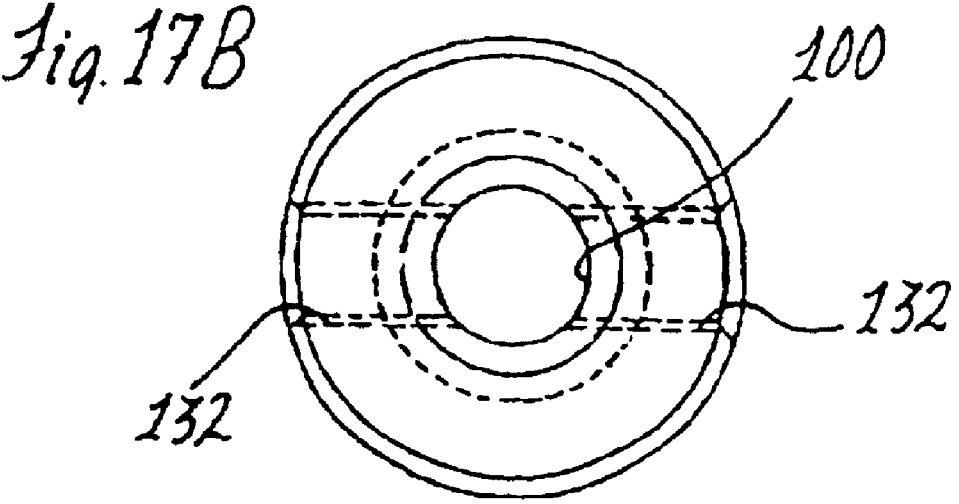
FIG. 17B is a plan view of the screw member of FIG. 17A showing an axial through opening of the cannulated screw member and the intersection between the through opening and the set screw transverse aperture.
Figure 20A:
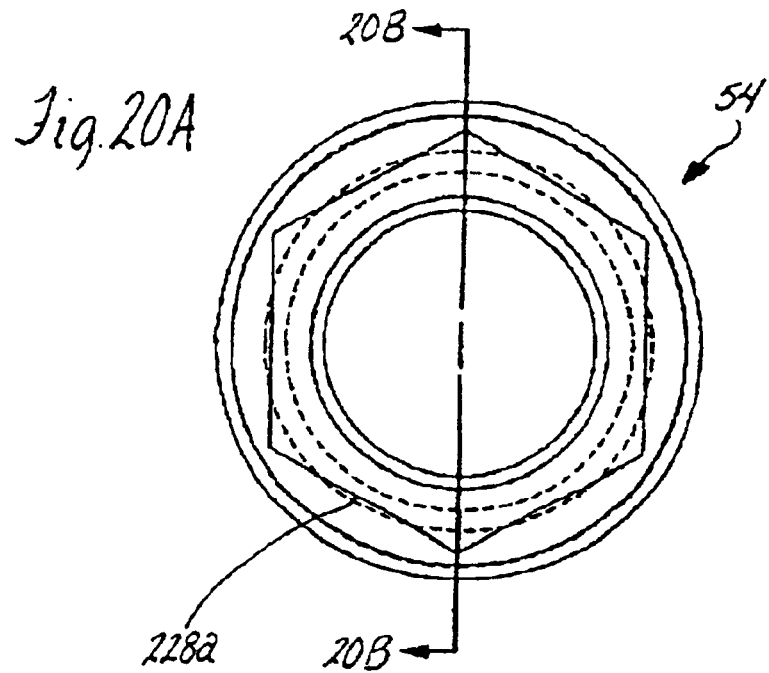
FIG. 20A is a front elevational view of the clamping nut of the rod mount assembly showing a hex driving surface thereof.
Figure 20B:
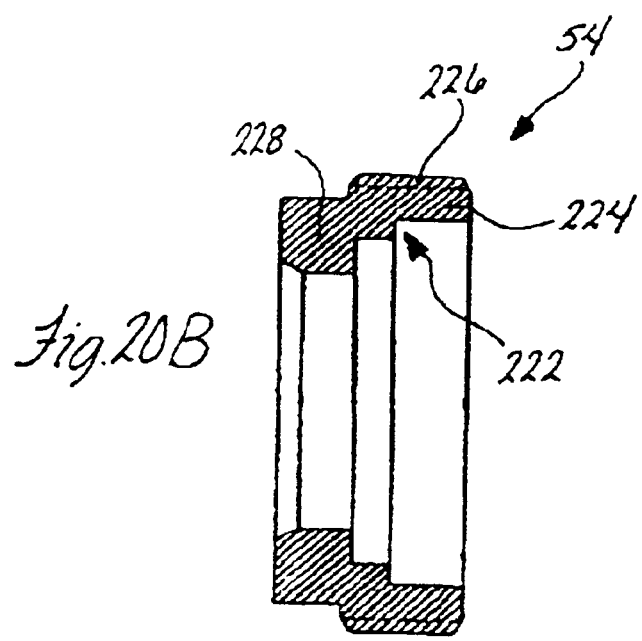
FIG. 20B is a cross-sectional view taken along line 20B—20B of FIG. 20A showing an externally threaded section of the clamping nut.

As referenced above, another advantageous feature employed in the preferred and illustrated fixators 12 for precision controlling engagement forces between the pins 18 and the bone 14 is the incorporation of a fine adjust device 90 to the pin advance assembly 32 which allows a user to fine tune the level of the engagement force between the pin end 38 and bone 14. As shown, the adjustment device 90 can be in the form of a screw device or member 92 having a threaded shank 94 and an enlarged proximal head 96 for turning the shank 94 about screw axis 92a, as can be seen in FIGS. 17A and 17B. The screw shank 94 of each of the screw members 92 is threaded into the housings 58 and 60 at the upper, internally threaded portion 98 of the respective throughbores 62–66 thereof. The screw shank 94 and head 96 have an axial throughbore 100 so that the screw member 92 is cannulated allowing the pin shaft 46 to pass therethrough with the proximal pin end 36 projecting out therefrom, as can be seen in FIGS. 8A and 8B.

Turning the screw head 96 to advance the shank 94 into the housing 58 causes the shank end 94a to engage the lever support block 70 extending transversely through one of the housing throughbores 64 and 66 via the transverse throughslots 68 thereof. In this regard, the generally cylindrical outer surface of the block 70 is provided with a flat 102 facing the screw device 92 for being engaged by the shank end 94a. With the shank end 94a engaged with the flat 102, continued turning of the screw head 96 causes the block 70 to be pushed downwardly against the bias force provided by the spring 72.

Pushing the block 70 with the screw shank 94 causes the pin 18 to be pushed therewith as the block 70 and the pin 18 are locked together via the engagement of the lever tooth 76 in the pin teeth 78 with the respective locking surfaces 40 and 44 in abutment as caused by the bias force of the spring 48 on the release lever 42. In this way, the turning or rotating action of the screw head 96 is translated into non-rotational, fine linear movements of the pin 18. Accordingly, turning of the screw device 92 can generate fine movements of the pin 18 much smaller than the ratcheting movements generated by pushing on the pin end 36. In other words, each ratcheted position of the pin 18 is defined in increments measured by the gap spacing 80 between each of the pin teeth 78 so that the initial ratcheting movement of the pin 18 will be coarser than the movements generated by turning of the screw device 92 which can be easily controlled by the user to be much smaller than the size of the gap spacing 80, e.g. approximately 0.063 inch. Thus, an initial stage of quick pin advance is provided by pushing on the pin end 36 for relatively larger advancing movements of the pin 18, with the final stage generating finer adjustments to the advancing movement of the pin 18 by turning of the screw device 92. Accordingly, in the preferred and illustrated form, the pin advance assembly 32 employs a two-stage application procedure for advancing and securing the bone pins 18 on the patient's bone 14.

The axial length of the slot 68 limits the travel of the follower block 70 therein from the proximate end 68a, to which the block 70 is normally biased, to the slot distal end 68b. With the follower block 70 at the distal end 68b of the slot 68, the screw device 92 can no longer advance the block 70 in the slot 68. However, the length of the slot 68 between the ends 68a and 68b thereof and size of block 70 provide approximately 0.300 inch of fine adjustment, which generally will be more than sufficient for obtaining the desired clamping force of the pin 18 on the bone 14. Since this maximum amount of fine adjustment is preferably the same or greater than the incremental advancing movements provided by ratcheting during the first stage of pin movements, if a user reaches the limit of fine adjustments, they can operate the release member 42 as will be described more fully hereinafter for allowing the pin 18 to be pulled away from the bone 14. Thereafter, the user ratchets the pin 18 to an advanced position that is beyond that to which they previously had ratcheted the pin 18, and operation of the fine adjust device 90 can proceed to provide the desired level of engagement force between the pin 18 and bone 14 without having the follower block 70 reaching the slot end 68b.

Figure 13A:
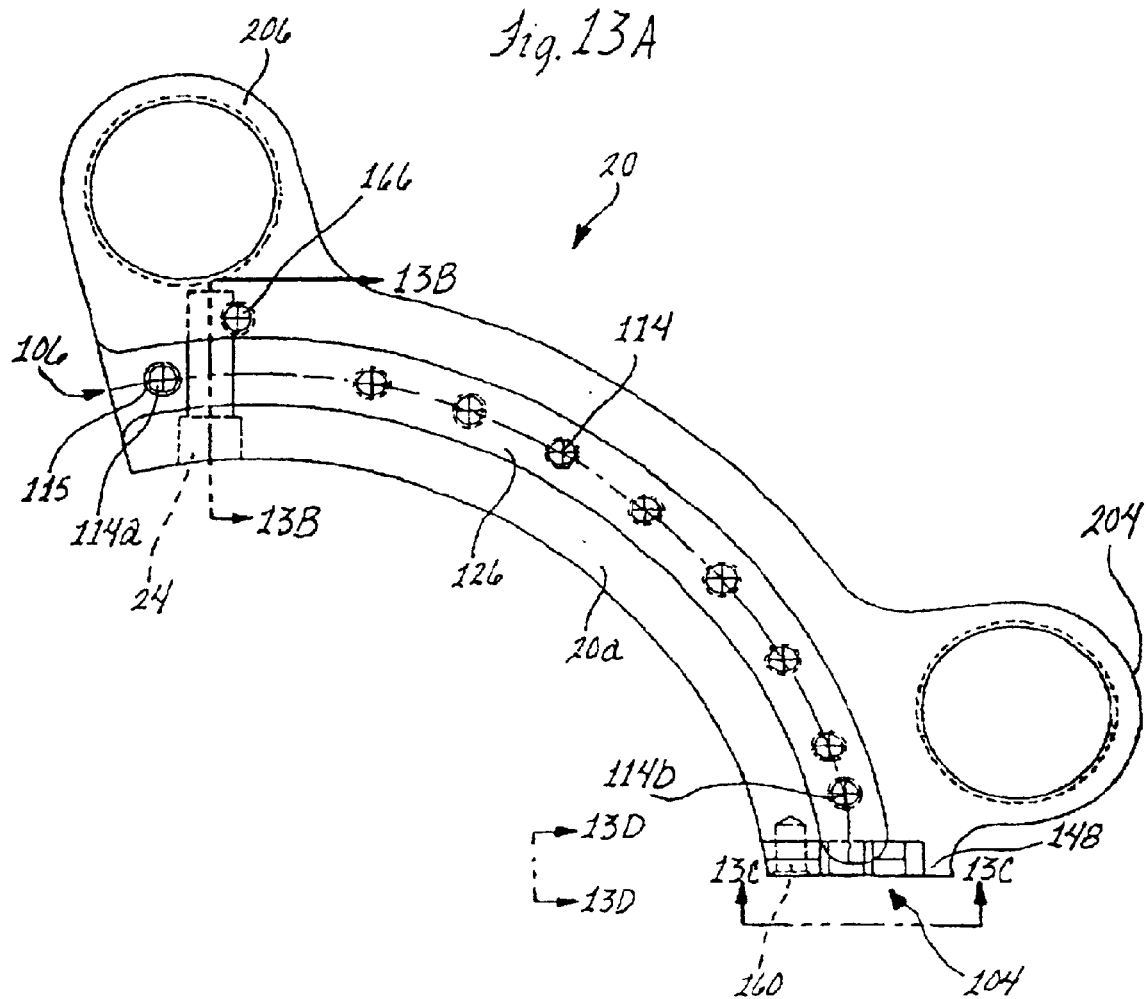
FIG. 13A is a side elevational view of the body of the female positioner member.
Figure 14B:
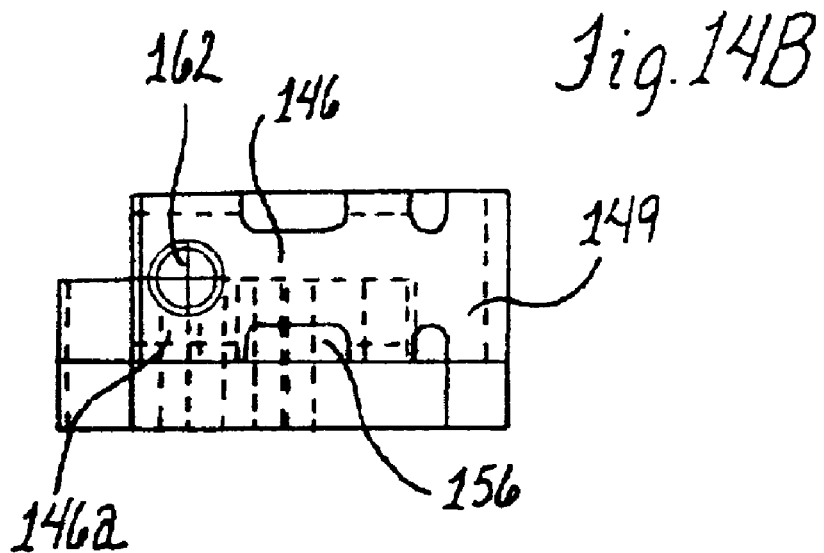
FIG. 14B is an end elevational view taken along line 14B—14B of FIG. 13A showing a mounting flange for the pin holder modules.

The preferred bone fixation system 10 herein utilizes a pair of pin positioner members 20 and 22 which include rigid bodies 20a and 22a, respectively, each having an arcuate configuration, as can be seen in FIGS. 13A and 14A, respectively. As shown, the body 20a extends in the general shape of an arch from one end 104 to its other end 106. Similarly, the positioner member body 22a extends in a general arch shape from one end 108 thereof to its other end 110. Both arch bodies 20a and 22a have similar arch shape configurations with generally the same radius of curvature, such as approximately 2.75 inches, so that when secured together via adjustable connection 112, the arch bodies 20a and 22a will cooperate to extend in a continuous arch shape from the end 104 of arch 28 to the end 108 of arch 22 at which the pin housing modules 58 and 60 are releasably mounted, which will be described further hereinafter. The arch bodies can also be provided in smaller and larger radius of curvature sizes, e.g. 1.75 inches and 3.75 inches, to accommodate smaller and larger patients. As illustrated, from end-to-end, arch body 20a extends for 104 degrees and arch body 20b extends 115 degrees.

Figure 15:
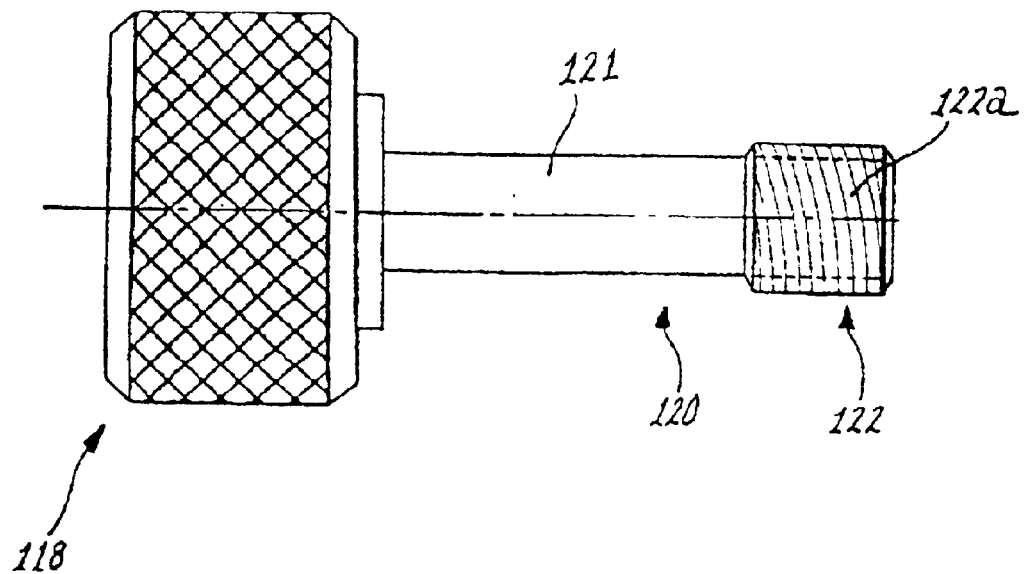
FIG. 15 is a side elevational view of a bolt member for adjustably securing the positioner member bodies together showing a small threaded section at a distal end of a shank of the bolt and an enlarged proximal head for turning of the bolt.

The preferred adjustable connection 112 includes a series of apertures 114 and 116 extending along the respective bodies 20a and 22a with at least one, and preferably two connecting members in the form of threaded bolts 118 threaded into aligned apertures 114 and 116 of the positioner member bodies 20a and 22a. As can be seen in FIGS. 3A and 4A, one connecting bolt 118a can be mounted in a partially threaded aperture 114a of the positioner member body 20a adjacent its end 106 with the other connecting member 118b being carried in a partially threaded aperture 116a of the positioner member body 22a adjacent its end 110. The remaining apertures 114 and 116 are substantially fully internally threaded, and the bolts 118a and 118b each include a shank 120 with a proximal non-threaded section 121 and distal threaded end 122 as shown in FIG. 15 for being threaded into the apertures 114 and 116 to connect the positioner members 20 and 22 in the position at which the bone pins 18 carried by the pin holders 28 and 30 are at the desired angular spacing from one another for being advanced into engagement with the bone 14 onto which the fixator 12 is to be secured.

The major diameter of the threads 122 is sightly greater than the outer diameter of the shank section 121 of the bolts 118. The apertures 114a and 116a in which the bolts 118 are carried include an enlarged counterbored portion 115 and 117, respectively, sized to allow the bolt threaded section 122 to be withdrawn into counterbore 115 and 117 and threaded to the partially threaded section of the apertures 114a and 116a to be held in clearance during sliding adjustment of the positioner bodies 20a and 22a between the various positions at which they can be secured together. In the preferred and illustrated form, there are seven adjustment apertures 114 spaced at ten degree intervals and one end aperture 114b spaced by five degrees from the adjacent aperture along the positioner member body 20a for being brought into alignment with adjustment bolt carrying aperture 116a of positioner member body 22a, and the positioner member body 22a has eight adjustment apertures 116 spaced at ten degree intervals therealong and one end aperture 116b spaced by five degrees from the adjacent aperture for being aligned with adjustment bolt carrying aperture 114a of positioner member body 20a. In this manner, the full angular range of adjustments between the preferred and illustrated positioner members 20 and 22 is between one-hundred and fifteen degrees where the bolt 118a is received in end aperture 116b and bolt 118b is received in end aperture 114b and starting at one-hundred and twenty degrees in ten degree increments to one-hundred and eighty degrees to provide eight different angular positions between the members 20 and 22.

As discussed above, the adjustable connection including the apertures 114 and 116 and connecting member 118 allow the positioner members 20 and 22 to be adjustably connected so that the bone pins 18 carried at the ends 104 and 108 thereof can have different angular spacings ranging from approximately 115 degrees (FIG. 4A) to approximately 180 degrees (FIG. 3) relative to each other. For adjusting the positioner members 20 and 22, a slide guide 124 is provided, as can be best seen in FIG. 3. The slide guide 124 can include an arcuate recess or groove 126 formed in the positioner member body 20a and an arcuate, raised rib or tongue 128 formed on the positioner member body 22a sized to fit in the recess 126. In this manner, there is a tongue and groove sliding fit between the positioner members 20 and 22 to allow them to slide between their various connected positions relative to each other. The above-described non-flat configuration of the members 20 and 22 is effective to increase their moment of inertia and thus their strength over prior flat arch members having a thin, substantially constant cross-sectional configuration. The generally U-shaped cross-sectional configuration of the female arch member body 20a and the generally T-shaped cross-sectional configuration of the male arch member body 22a via the provision of the recess 126 and rib 128 thereon, respectively, increases their rigidity adding further stability to the present fixation system 10.

As can be seen in FIGS. 13A and 14A, the female arch body 20a has its recess 126 formed centrally thereon with the apertures 114 extending therethrough. Likewise, the male arch member body 22a has the raised rib 128 formed centrally thereon with the apertures 116 extending therethrough. While the arch members 20 and 22 can be slid apart, it is preferred that the slide guide 124 incorporate retaining flanges and cooperating recesses (not shown) that keep the arch members 20 and 22 together when they are being slid without separating in direction away from each other transverse to the sliding direction.

Returning to more of the details, the pin advance assembly 32 preferably includes a further locking mechanism associated with the fine adjust device 90. In the preferred form, the locking mechanism includes a set screw, and most preferably two set screws 130 that are threaded into transversely extending, diametrically opposite apertures 132 formed in the turning head 96 of the fine adjust screw member 92, as can be seen in FIGS. 17A and 17B. The apertures 132 communicate with the through bore 100 of the cannulated screw member 92 through which the pin shaft 46 extends. Accordingly, once the desired level of clamping force between the pin 18 and bone 14 is achieved by turning of the fine adjust device 92, the user advances the set screws 130 through the apertures 132 until surfaces at the screw distal ends 130a are tightened into engagement with the surface of the pin shank 46. The tightening of the screws 130 onto the pin shaft 46 locks the pin 18 in position.

Figure 10A:
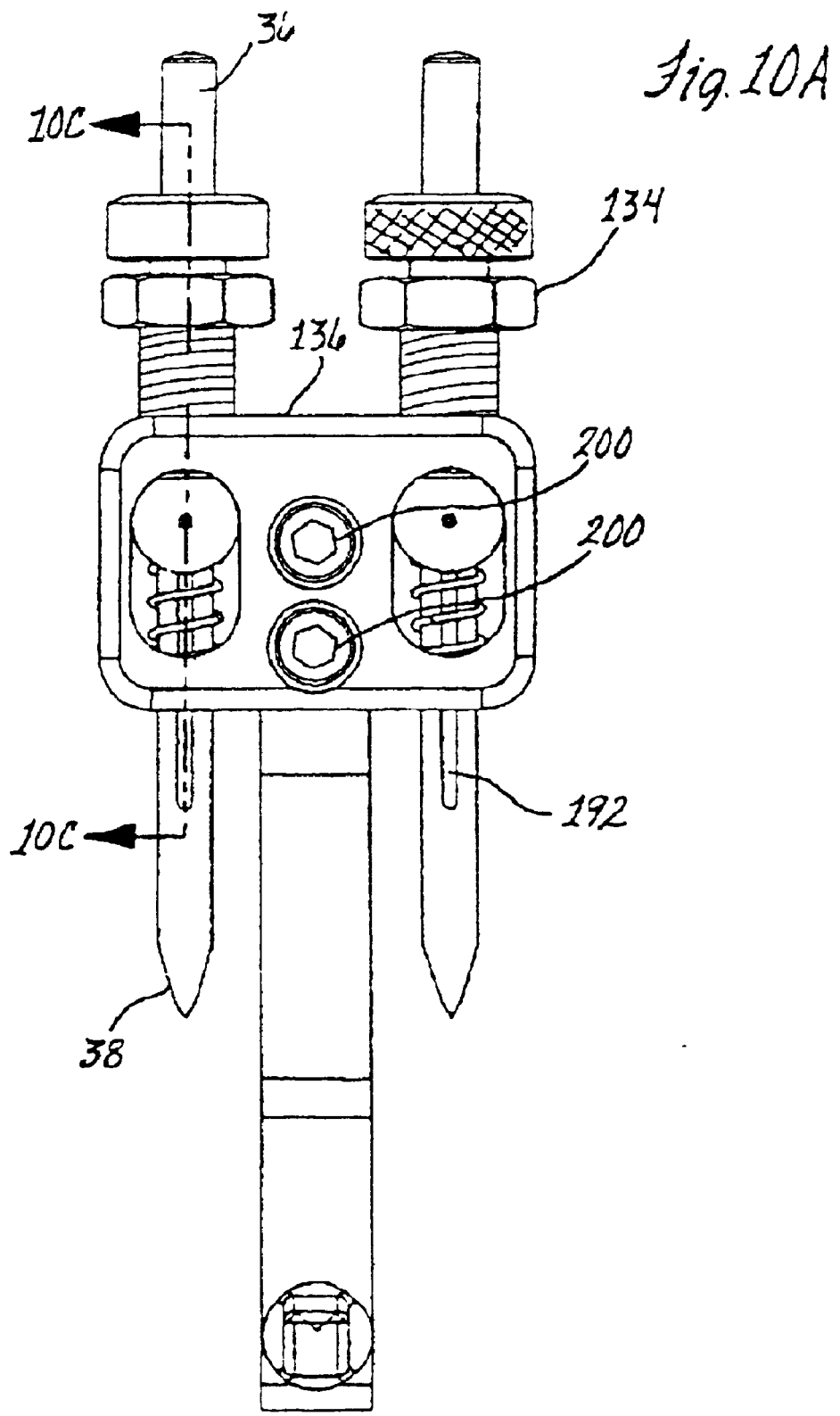
FIG. 10A is a front elevational view of an alternative bone fixator having a stop nut threaded to the fine adjust screw member for locking the advanced position of the pin in place, and having a fixed bone pin at an opposite end thereof.

An alternative locking mechanism for the fine adjust device 92 is shown in FIGS. 10A–10C which employs a lock or jam nut 134. The jam nut 134 is threaded onto the shank 94 of the cannulated screw 92, and is threaded down into tight engagement with the top surface 136 after the fine adjust screw member 92 has been utilized to achieve the desired level of engagement force between the pin 18 and the bone 14 for locking the pin 18 in place. The jam nut locking mechanism is less preferred than the set screw locking mechanism as it generally requires that the cannulated screw member 92 of the fine adjust device 90 have a longer shank 94 to accommodate the jam nut 134 threaded thereon. The set screw locking mechanism allows the screw shank 94 to be smaller thus keeping the overall size of the housing modules 58 and 60 to a minimum, including the fine adjust screw member 92 projecting beyond the housing top surface 136 thereof.

Figure 16A:
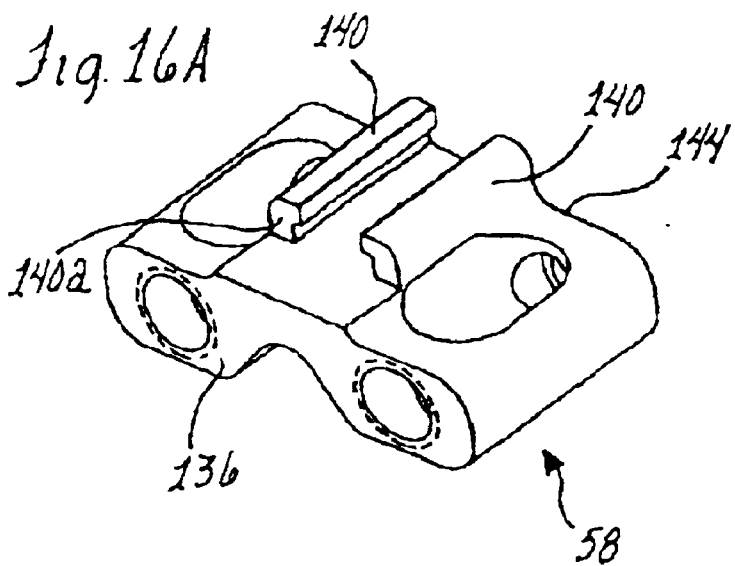
FIG. 16A is a perspective view of a housing of the pin holder module.
Figure 16B:
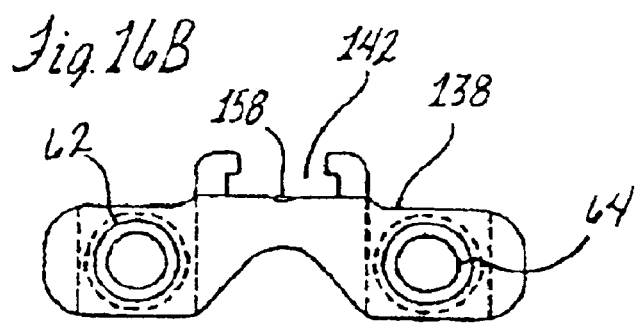
FIG. 16B is an end elevational view of the housing of FIG. 15A showing mounting flanges and a pair of through openings through which a pair of pins are received.
Figure 16C:
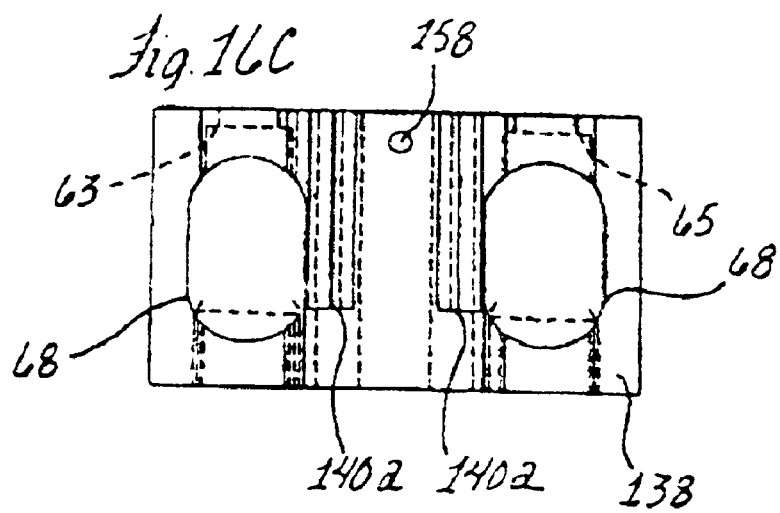
FIG. 16C is a side elevational view of the pin holder module housing showing a pair of fine adjust travel limiting slots and a recess for receipt of the detent ball of the positioner bodies.

The preferred pin housing modules 58 and 60 and positioner members 20 and 22 have a releasable attachment formed between the back surface 138 of the housings 58 and 60 and the ends 104 and 108 of the respective positioner member bodies 20a and 22a. As best seen in FIGS. 16A–16C, with respect to housing 58, the housings 58 and 60 each include opposing mounting flanges 140 projecting rearwardly from surface 38. With the housing 58, the flanges 140 are disposed between the pair of through slots 68 and each include a generally L-shaped configuration so as to define a T-slot 142 therebetween. The opposing flanges 140 extend along the rear surface 138 of the housings 58 and 60 from the bottom surface 144 thereof and terminate at their ends 140a short of the housing top surface 136.

Figure 13B:
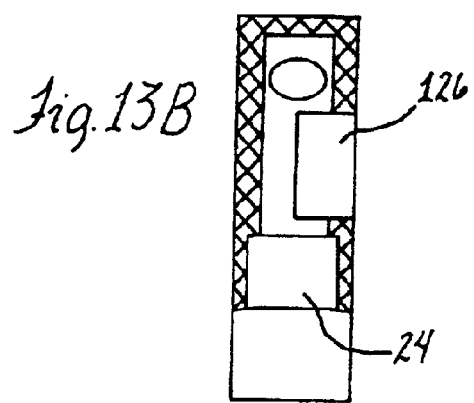
FIG. 13B is a cross-sectional view taken along line 13B—13B of FIG. 13A showing the depth of the groove in the body and a pin receiving aperture.
Figure 13C:
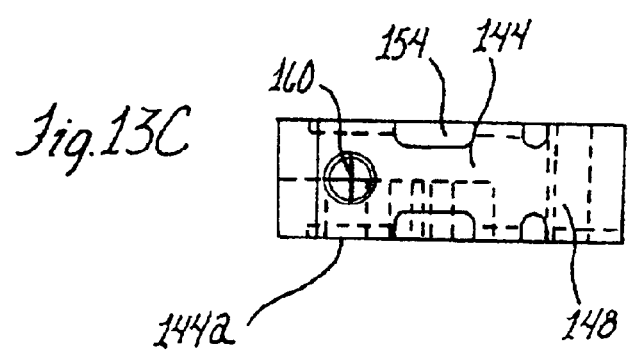
FIG. 13C is an end elevational view taken along line 13C—13C of FIG. 13A showing a mounting flange for the pin holder module.
Figure 13D:
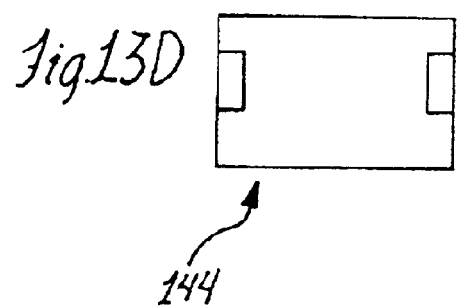
FIG. 13D is an elevational view taken along line 13D—13D of FIG. 13A showing the T-shaped configuration of the mounting flange.
Figure 14C:
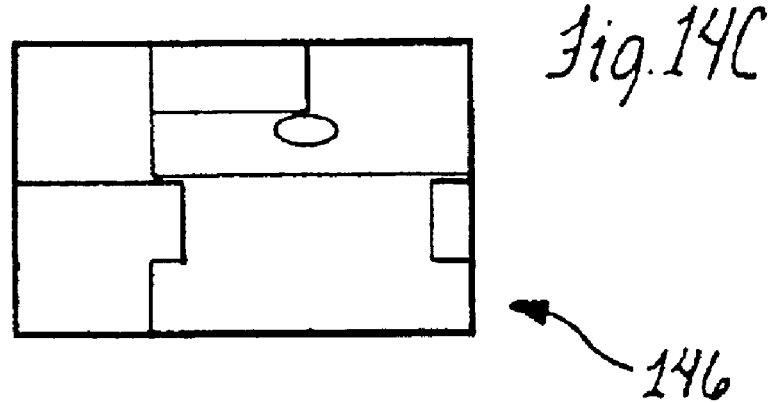
FIG. 14C is an elevational view taken along line 14C—14C of FIG. 14A showing the T-shaped configuration of the mounting flange.

Referring to FIGS. 13C and 13D, it can be seen that the end 104 of the positioner member body 20a has a raised flange 144 having a T-shaped configuration to provide a slide fit into the T-slot 142 formed by the opposing flanges 140. Similarly, referencing FIG. 14B and 14C, the positioner member body 22a has a T-shaped mounting flange 146 formed at its end 108 for providing a sliding fit between the opposing flanges 140 and the T-slot 142 formed therebetween of the housing modules 58 and 60. Both of the T-mounting flanges 144 and 146 terminate at a back wall 148 and 149, respectively, against which the ends 140a of the flanges 140 abut to locate the housing modules 58 and 60 in a predetermined position on the ends 104 and 108 of the respective positioner member bodies 20a and 22a.

Figure 4B:
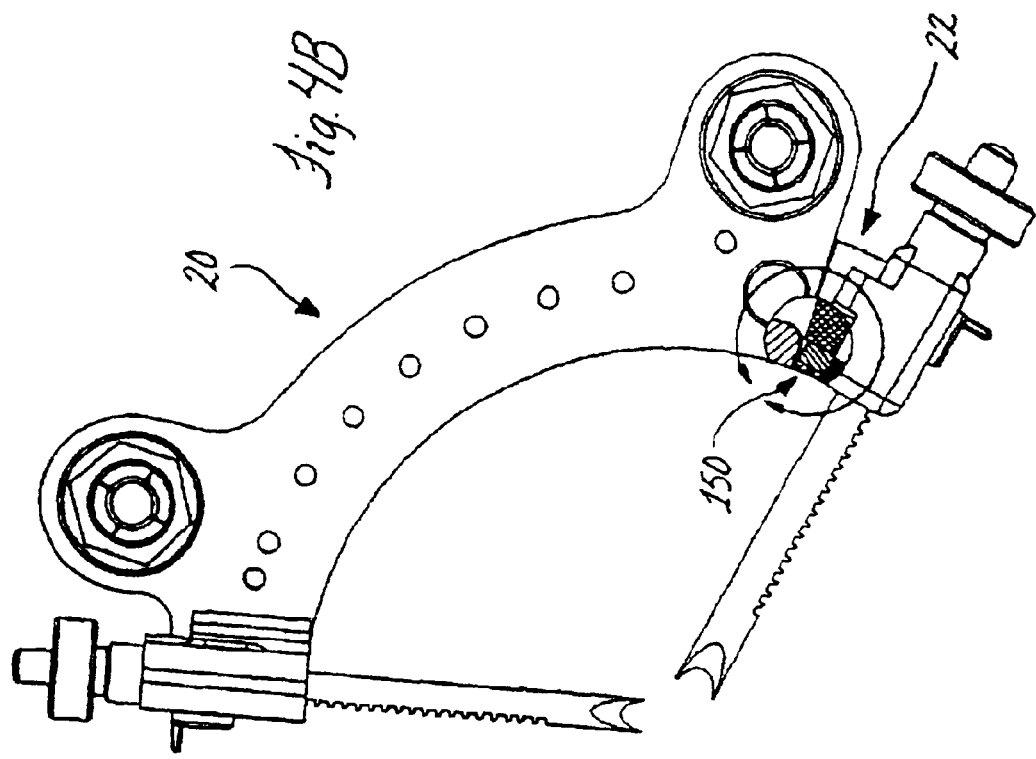
FIG. 4B is a side elevational view of the bone fixator partially sectioned to show a releasable connection between a pin holder module and the end of the pin positioner member supporting the single pin thereat.
Figure 4C:
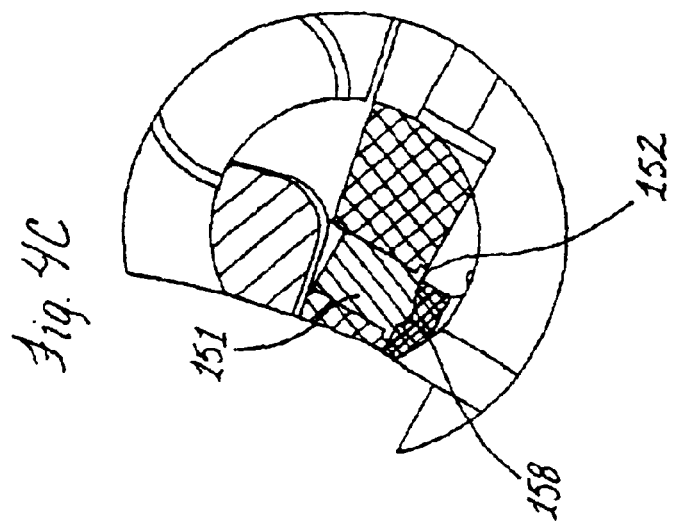
FIG. 4C is an enlarged view of the partially sectioned portion of FIG. 4B showing a detent ball disposed in a recess of the module.

To secure the housing module 60 on the ends 104 or 108 of the positioner member bodies 20a and 22a against sliding back out therefrom, a detent 150 is provided between the positioner member ends 104 and 108 and the housing module 58 or 60, as best seen in FIGS. 4B and 4C. The detent 150 can include a plunger ball 151 mounted to the body ends 104 and 108 so that arcuate surface 152 of the ball 150 projects beyond respective lowered flat surfaces 154 and 156 formed at the body ends 104 and 108. The holder modules 58 and 60 each include a recess 158 formed centrally between the flanges 140 in the rear surface 138 thereof adjacent the housing bottom surface 144. The ball 151 is mounted in apertures 160 and 162 formed in the respective body surfaces 154 and 156 adjacent forward ends thereof spaced forwardly from the rear walls 148 and 149. In this regard, the flanges 144 and 146 each include respective upper forward portions 144a and 146a that overhang the lowered surfaces 154 and 156 above the detent balls 151 at the positioner body ends 104 and 108, respectively.

Thus, to mount the modules 58 and 60 to the positioner member bodies 20a and 22a, the user slides the housing modules 58 and 60 onto the ends 104 and 108 of the respective bodies 20a and 22a, and when the housing modules 58 and 60 reach their predetermined position as by abutment of their flange ends 140a against the rear walls 148 and 149, the detent ball 150 will resiliently rebound from a recessed position where the arcuate surface 152 is flush with the lowered surfaces 154 and 156 to its extended position with the arcuate surface 152 received in the recess 158 of the housing modules 58 and 60. In this manner, the holders 58 and 60 are releasable secured to the positioner bodies 20a and 22a. To take the holder modules 58 and 60 off of the bodies 20a and 22a, the user simply reverses the sliding action, pulling the housing modules 58 and 60 forwardly with the detent ball 151 camming back into the aperture 160 and 162 in which it is mounted. Thus, the above-described releasable attachment provides for tooless mounting and demounting of the modules 58 and 60 to the positioner members 20 and 22. When the bone pins 18 are advanced into clamping engagement with the bone 14, the reactive forces provided back up along the pin shank 46 and taken by the engaged locking surfaces 40 and 44 will keep the modules 58 and 60 securely pushed up against the body walls 148 and 149. Accordingly, the detent 150 is not relied upon to provide the securing force between the modules 58 and 60 and the position bodies 20 and 22 when in use.

By way of the above-described modularity provided to the pin holders 28 and 30, the bone fixators 12 herein are provided with a significant degree of flexibility in allowing a user to select the specific type of bone pin and the number of bone pins for use in a particular bone fixation procedure. As shown, the typical procedure will involve utilizing the three-point clamping of the fixator 12 to the bone 14 with the double pin module housing 58 releasably secured to the positioner member end 104, and the single pin module 60 releasably secured to the positioner member end 108. In addition, the adjustability of the female and male positioner members 20 and 22 to each other allows this three-point clamping action to be obtained at various angles of relative orientation between the pins 18 of the respective modules 58 and 60, as previously discussed.

As is apparent, the modules 58 and 60 could be reversed with single pin module 60 releasably mounted to the female positioner member 20, and the dual pin module 58 releasably mounted to the male positioner member 22. In other applications, four-point or two-point clamping action may be desired and either a pair of the dual pin housing modules 58 or a pair of the single pin housing modules 60 can be employed. Further, each of the modules 58 and 60 can be provided with different types of bone pins 18 such as with differently configured bone engaging ends 38 and/or different lengths and diameters of bone pins. Manifestly, the present fixators 12 provide significant flexibility to the user with the wide range of pin orientations that can be obtained, as well as the number and type of pins that can be selected for use.

Referring to FIG. 5, the option of simply utilizing a single one of the positioner members is illustrated with respect to the positioner member 20 to allow the pins 18 to be oriented at a ninety degree separation from each other. In this regard, the positioner member body 20a is provided with the aperture 24 for receiving the fixed pin 26 therein, as previously described. The aperture 24 is formed on inner curved surface 164 of the body 20a adjacent the end 106 thereof, as can be seen in FIGS. 13A and 13B.

A threaded aperture 166 is formed in the body 20a to extend transversely to and intersect with the pin receiving aperture 24. The aperture 166 is spaced from the curve of the set of adjustment apertures 114 so that it is not formed in the recess 126 of the arch member body 20a. The aperture 166 is sized the same as aperture 114a so that the connecting member 118a carried in the aperture 114a which is no longer necessary for securing the body 20a and 22a together can be threaded into the aperture 166. With the pin 26 received in the aperture 24, the fastener 118a is advanced through the aperture 166 until its end is brought into tight engagement with the shank of the fixed pin 26 residing in the aperture 24. In this manner, the pin 26 is tightly secured to the positioner member body 20a in fixed position relative thereto.

As can be seen best in FIG. 5, the fixed pin 26 has a distinctly configured bone-engaging end 168 including a plurality of prismatic prongs 170 for tight gripping on the bone 14. When using the ninety degree spacing between the pin 18 with only the positioner member 20 employed as shown in FIG. 5, the user generally will orient the pair of pins 18 so that they engage on the anterior ridge 81 or anterior surface 82 of the tibia, with the fixed pin 26 secured at its distal end 168 with the posterior surface 86. Because this surface 86 is typically concealed or difficult to view, the pin 26 is provided with a raised shoulder 172 spaced rearwardly from the prongs 170 which will be advanced into abutment with the bone 14 with the prongs 170 in clearance therefrom to provide the user with a tactile feel of when the pin 26 is in proper position for advancing the pins 18 to clamp the bone 14 between the displaceable pin ends 38 and the fixed pin end 168.

The release lever 42 and the support block 70 therefor will next be described in more detail. Referring to FIGS. 18A–18D, it can be seen that the lock has a transverse slot 174 that extends from the through opening 74 to front 176 of the support block 70. The lever 42 has a transverse handle portion 178 and a leg portion 180 having a juncture 182 therebetween. The handle and leg portions 178 and 180 generally extend at right angels to each other and are pivotally mounted via the pivot pin that is pressed into apertures 184 formed on either side of the slot 174. The lever 42 likewise has an opening formed at the juncture 182 of the handle and leg portions 178 and 180 through which the pivot pin 80 extends and about which the lever 42 is pivotal.

The slot 174 is partially closed by wall portion 186 at the front 176 of the support block 70. The portion 186 terminates at its upper end 186a short of the flat 102 to leave an access opening 188 to the slot 174. The handle portion 178 of the lever 42 projects in the slot 174 and out therefrom through the opening 188. The spring 48 that biases the tooth 76 into engagement with the pin teeth 78, is disposed between the wall 186 and the back of lever leg portion 180.

The leg portion 180 of the lever 42 extends into the through opening 74 of the support block 70 and is biased with a predetermined bias force by the spring 48 so that the tooth 76 at the end of the leg portion 180 engages in the rack of cam teeth 78 formed along the bone pin shaft 46, as previously described. To allow the bone pin 18 to be shifted in a retracting direction opposite to the advancing direction 33, the fine adjust screw device 92 is turned so that it does not press down on the support block flat 102 with its end 104a to provide some freedom of movement at the pin distal end 38 by way of the the retraction direction bias provided by spring 72. If the fine adjust locking mechanism either in the form of the set screws 130 or the jam nut 134 is in the locking mode, the locking mechanism is disengaged to allow turning of the screw device 92. This enables the operator to utilize the lever portion 178 projecting out of the support block 70 through the access opening 188 to be pivoted in the direction indicated by arrow 190 in FIG. 10C against the bias provided by spring 48. Once the lock surface 40 on the lever tooth end 76 clears the bone pin teeth 78, and particularly the adjacent lock surface 44 thereof, the bone pin 18 can be shifted in the retracting direction.

Pivoting of the handle portion 178 in pivot direction 190 also allows the spring 72 to bias the support block 70 to the proximate end 68a of the housing slot 68. The support block 70 includes an outer annular seat 191 formed about the bottom of the through opening 74 sized to receive the upper coil of coil spring 72 therein, as shown in FIGS. 18B and 18D. The lower coil of each of the springs 72 rests against the inner shoulder 63 and 65 of the bottom 144 of the housing 58 about the bottom opening to the respective housing throughbores 62 and 64 so that the spring 72 exerts a bias force on the block 70 urging it toward the slot end 68a. Accordingly, when the user pivots the lever 42 to disengage the lever tooth 76 from the pin teeth 78, the spring 72 biases the block 70 into engagement with the slot proximal end 68a.

The bone pins 18 are provided with an elongate narrow groove 192 in which support block pin 194 travels, as can be seen best in FIGS. 10A and 10C. Referring to FIG. 19C, it can be seen that the groove 192 has its proximal end 192a at a point slightly beyond the most proximal pin tooth 78 whereas the distal end 192b of the groove 192 is generally aligned with the distal most pin tooth 78. The pin 194 is pressed into aperture 196 formed in rear wall 198 of the block 70 so that the pin 194 extends into the through opening 74 and into registry with the pin groove 192. The bone pin groove 192 and the dowel pin 194 prevent the bone pin 18 from rotating in the through opening 74 keeping the bone pin teeth 78 in facing relation with the lever tooth 76 for engagement therewith. In addition, when pulling the pin in the retracting direction, the slot end 192b serves to limit the amount of retraction that the bone pin 18 can undergo. Slot end 192a prevents the pins 18 from falling out the housings 58 and 60.

FIGS. 10A–10C are directed to a bone fixator 12a that has a slightly differently configured arch member 199 (FIG. 10B) that is adapted to be used in a fixed, ninety degree orientation of its pins 18 and 26. The arch member 199 has three linear sections angled to each other to provide the ninety degree spacing of the pins 18 and 26. The arch member 199 has a pin housing, similar to housing 58 except that it is fastened to one of the arch ends 199a as by bolts 200, and the fixed pin 26 has a releasable attachment to the other end 199b of the arch 199 including a screw member 201 inserted through a rear opening in the arch member 199 and threaded to a tapped opening 202 at the rear of the shaft 203 of the pin 26. This allows different pins 26 to be interchanged for being fixed to arch member 199. Another difference lies in the orientation of the housing 58 secured to the arch 199. As best seen in FIG. 10B, the bone pin teeth 78 face toward the arch 199. Referring to FIGS. 1–3, the housing 58 is shown as being switched in terms of its attachment orientation relative to the positioner member 20. In this regard, the pin teeth 78 of the pins 18 all face outwardly away from the body 20a. Since the reaction forces along the pins 18 when applied in clamping engagement on a bone 14 are all directed toward the positioner bodies 20a and/or 22a, by having the pin teeth 78 in their preferred outwardly facing orientation, a potential source of weakness in the pin shafts 46, i.e. the cut teeth 78 formed therealong, are positioned so that stress concentrations thereat are minimized.

The rod mount assemblies 52 will next be described in more detail. Referencing FIGS. 11A–11D and FIG. 13A, it can be seen that the rod mount assemblies 52 are mounted to enlarged flange portions 204 and 206 formed integrally with the positioner member body 20a. More specifically, the flange portions 204 and 206 have a generally annular configuration and are internally threaded for receiving the clamping nuts 54 therein. The clamping ball 56 preferably has a spherical configuration and has a through bore 208 formed therein through which the connecting rods 16 can extend. The clamping ball 54 has a plurality of circumferential slits 210 formed therealong which allows the ball 210 to be compressed via the clamp nut 54 so that the bore walls 208 are tightly engaged on the connecting rod 16 for fixing it in the rod mount 54.

Figure 21A:
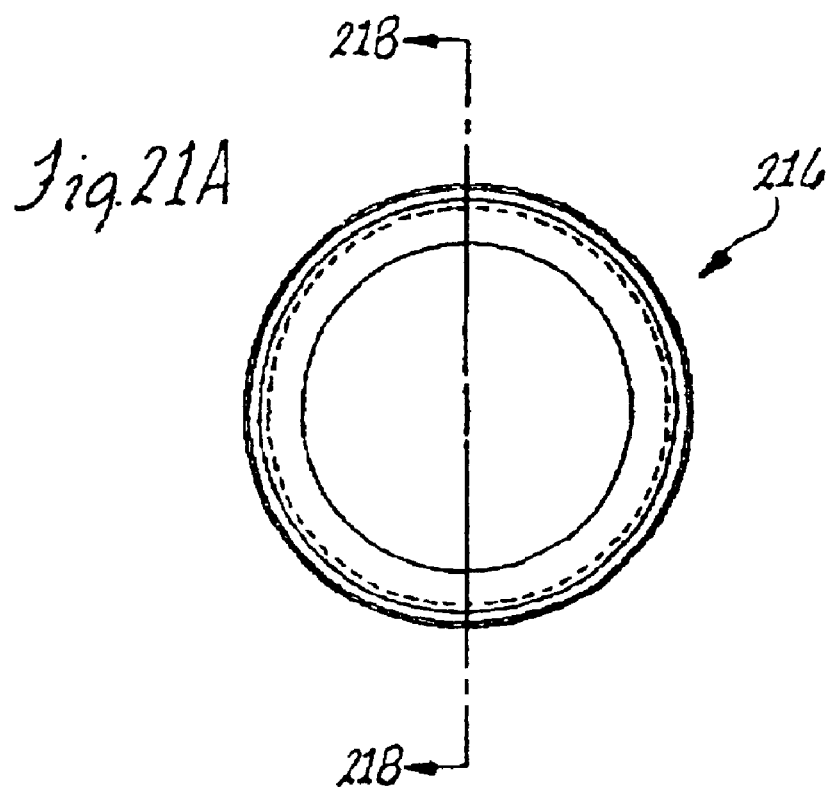
FIG. 21A is a front elevational view of a ball holder ring that fits between the clamping nut member and the resilient ball of the rod mount assembly.
Figure 21B:
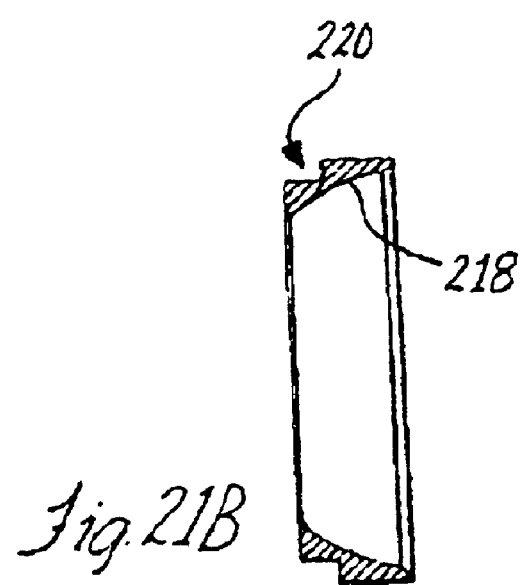
FIG. 21B is a cross-sectional view taken along line 21B—21B of FIG. 21A shows an internal arcuate surface of the holder member of FIG. 21A to conform to the configuration of the resilient ball.
Figure 22A:
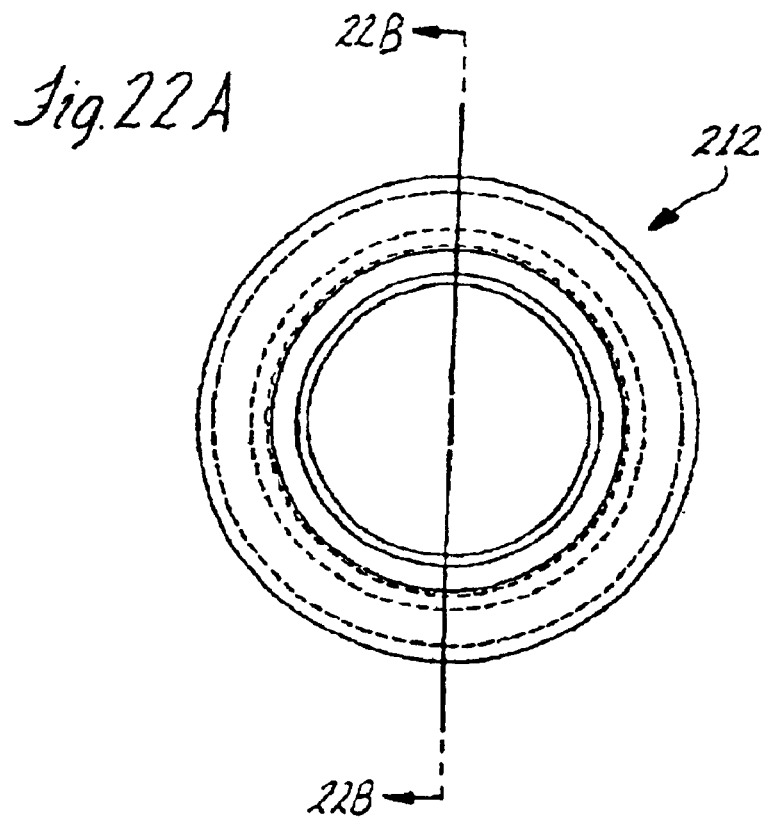
FIG. 22A is a rear elevational view of the stationary ball holder member.
Figure 22B:
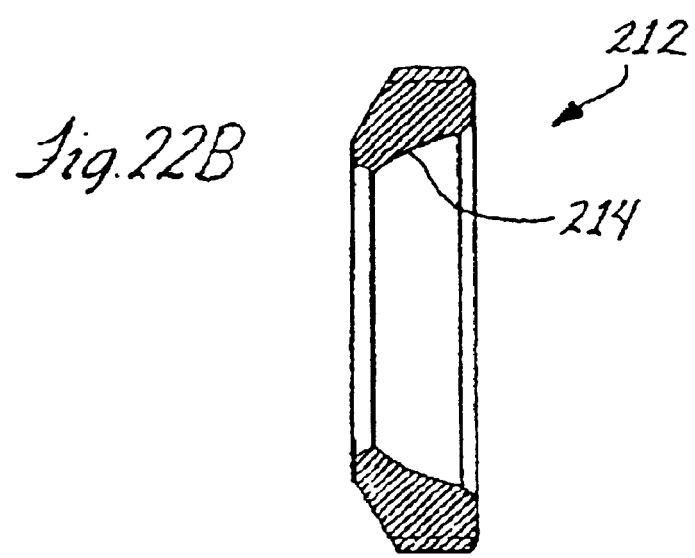
FIG. 22B is a cross-sectional view taken along line 22B—22B of FIG. 22A of the stationary ball holder member showing an internal arcuate surface for conforming to the resilient clamping ball.

A ball holder nut 212 is threaded into the annular flange portions 204 and 206 and is provided with an arcuate inner surface 214 that generally conforms to the spherical shape of the clamping ball 56, as shown in FIGS. 22A and 22B. Accordingly, with the holding nut 212 threaded in the flanges 204 and 206, the spherical clamping balls 56 are seated against the inner surface 214 thereof At the other end of the ball 56 and between it and the clamping nut 54 is a bearing ring 216 which also has an arcuate inner surface 218 configured to conform to the spherical ball 56, as can be seen in FIGS. 21A and 21B. The ring 216 has an outer stepped surface 220 for interfacing with a corresponding inner stepped surface 222 of the clamping nut 54. The inner stepped surface 222 is formed internally on a threaded portion 224 of the nut 54 having external threads 226 formed thereon. A hex driving flange 228 is integral with the threaded portion 222 adjacent thereto and has a plurality of hex surfaces 228a formed about its periphery for being engaged by an appropriately configured driving tool.

Accordingly, as shown in FIG. 11B, with the bore 228 in its substantially fully opened configuration, the connecting rods 16 are inserted in the rod mounts 54. To secure them in clamped position, the clamping nut 54 is advanced by turning thereof via the drive surfaces 228a so that the inner stepped surface 222 of the nut 212 engages the outer stepped surface 220 of the ring member 216 driving its arcuate surface 218 toward the stationary holder nut 212 and the arcuate surface 214 thereof. This relative shifting between the surfaces 214 and 218 compresses the resilient clamping ball 56 via the compression slits 210 thereof for clamping the bore walls 208 down into tight engagement with the portion of the clamping rods 16 extending therethrough.

Figure 12B:
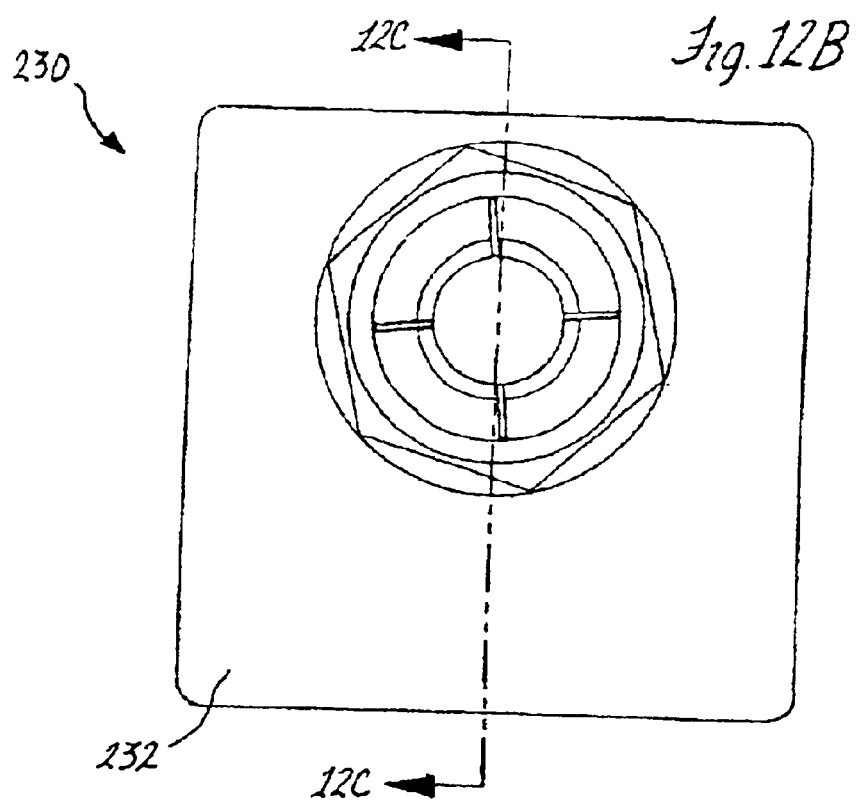
FIG. 12B is a front elevational view of one of the rod mounts detached from the positioner member body.
Figure 12C:
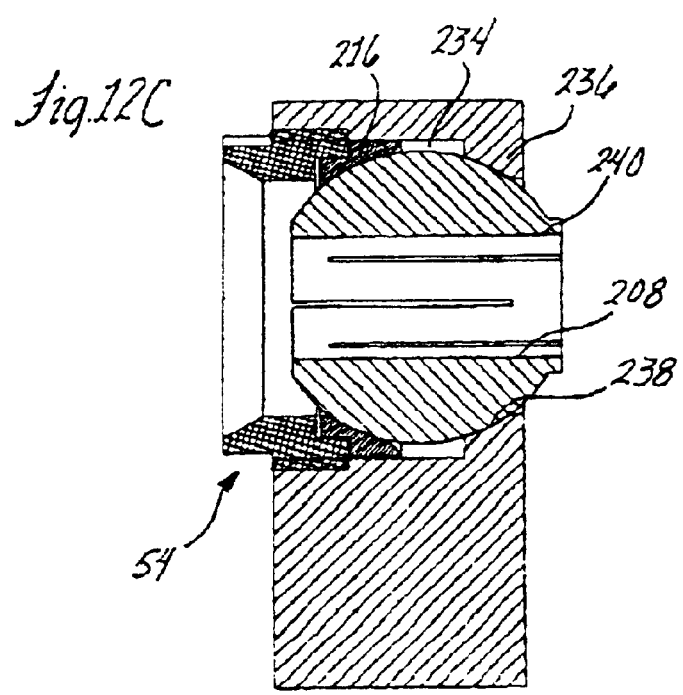
FIG. 12C is a cross-sectional view taken along line 12C—12C of FIG. 12B showing the rod mount assembly including the resilient ball having a locating portion to keep the through opening therethrough accessible for receipt of connecting rods.

Attaching individual rod mounts 52 onto the arch members 20 and 22 is also contemplated so that a pair of interconnected fixators 12, for example, can be connected by additional rods 16 to another fixator or fixators which themselves can be interconnected by connecting rods 16. Referring to FIGS. 12A–12C, rod mount modules 230 are shown each including rod mounts 52, substantially as previously described. The modules 230 include a block 232 having a generally cylindrical opening 234 in which the rod mount 52 is received. Instead of the holding nut 212, the module block 232 is configured with a wall portion 236 having an arcuate surface 238 that conforms to the configuration of the spherical ball 56, as can be seen in FIG. 12C. In all other respects, the modules 230 employ the same rod mounts 52 as previously described including a clamping nut 54 and a bearing ring member 216.

As mentioned, the clamping balls 56 have a generally spherical configuration. It is preferred that the clamping balls 56 include a radially extending locating portion 240 that extends about one end of the bore opening 208 so that at the radially extending portion 240, the clamping ball 56 deviates from the general spherical configuration thereof. In this manner, should the clamping ball 56 rotate while held between the surfaces 214 and 218 prior to being clamped onto a rod 16, the locating portion 240 will prevent the bore opening 208 from shifting to the point where the rod 16 cannot be inserted therein. In other words, should the ball 56 rotate, the of the pin advance assembly 32. However illustrated, the pin advance assembly 240 is generally less preferred as it will typically require two-handed operation with the user's one hand gripping the positioner and pushing on the pin end 36 while the other hand is depressing the button 244 during the initial quick advance stage of application of the bone pins 18 to the bone 14. It is contemplated that the button 244 can be locked in its depressed position to enable one-handed pin application as has been described with respect to pin advance assembly 32.

While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention.

We claim:

1. A fixation apparatus for being fixed to a bone to keep the bone in a fixed position relative to the apparatus during a healing process therefor, the fixation apparatus comprising:

at least one bone pin having a proximal end and a distal tip end configured for tightly gripping onto the bone;

a pin positioner that supports the pin to allow a user to manipulate the positioner external of a patient's body for positioning the pin to be advanced into engagement with the bone;

a pin holder of the positioner for carrying the pin and having a pin advance assembly operably connected to the pin to allow a user to shift the pin in an advancing direction to bring the distal tip end into gripping engagement with the bone, the pin advance assembly being integrated with the pin holder for staying with the positioner during the healing process;

a housing of the pin holder mounted to the pin positioner and having an opening extending in the advancing direction; and a support member of the pin advance assembly through which the pin extends for being advanced therethrough with the support member disposed in the housing opening and the pin advance assembly being operable to shift the support member together with the pin in the housing opening in the advancing direction for advancing the pin therewith.

2. The fixation apparatus of claim 1 wherein the pin advance assembly includes a locking mechanism locking surfaces which allow the user to shift the pin to an engaged position with the bone with the locking surfaces engaged to substantially keep the pin from shifting in a retracting direction opposite the advancing direction and away from the engaged bone.

3. The fixation apparatus of claim 1 wherein the pin advances assembly includes a ratcheting mechanism between the pin holder and the pin which substantially keeps the pin from shifting away from the advanced position thereof.

4. The fixation apparatus of claim 1 wherein the pin holder housing has a through opening with the pin proximal end projecting out from the housing opening, and the pin advance assembly includes cam surfaces that allow a user to push on the pin projecting proximal end for shifting the pin in the advancing direction thereof and providing the user with optimal tactile feedback on secure engagement between the pin distal tip end and the bone.

5. The fixation apparatus of claim 4 wherein the pin advance assembly includes a lever, and stop surfaces and the cam surfaces being on the lever and the pin, and a biasing mechanism that urges the stop and cam surfaces together with a predetermined bias force so that pushing the pin proximal end causes the lever to shift against the bias force with the bias force sufficient to keep the pin from retracting away from the bone upon release of the pin.

6. The fixation apparatus of claim 1 wherein the pin positioner and the pin holder include a releasable attachment therebetween, and the pin holder comprises modules that carry one or multiple pins and pins of different sizes which allows a user to select the number and size of bone pins to be carried by the positioner.

7. The fixation apparatus of claim 1 wherein the pin positioner comprises a plurality of rigid members having a plurality of fixed positions relative to each other to allow the associated pin holders to be oriented at various different positions relative to each other about the bone to obtain different angles of orientation for the bone pins carried thereby relative to the bone.

8. The fixation apparatus of claim 1 wherein the pin advance assembly includes a fine adjustment device operable to advance the pin with fine force adjustments and with high resolution feedback of pin-to-bone engagement forces to the user.

9. A fixation apparatus for being fixed to a bone to keep the bone in a fixed position relative to the apparatus during a healing process therefor, the fixation apparatus comprising:

at least one bone pin having a proximal end and a distal tip end configured for tightly gripping onto the bone;

a pin positioner that supports the pin to allow a user to manipulate the positioner external of a patient's body for positioning the pin to be advanced into engagement with the bone; and a pin holder of the positioner for carrying the pin and having a pin advance assembly operably connected to the pin to allow a user to shift the pin in an advancing direction to bring the distal tip end into tripping engagement with the bone, the pin advance assembly being integrated with the pin holder for staying with the positioner during the healing process;

wherein the pin positioner and the pin holder include a releasable attachment therebetween, and the pin holder comprises modules that carry one or multiple pins and pins of different sizes which allows a user to select the number and size of bone pins to be carried by the positioner;

wherein the pin positioner comprises at least one rigid member having opposite ends, and the releasable attachment includes interengaging mounting flanges of at least one of the ends of the positioner member and the pin holder module for mounting the module at a predetermined position on the rigid member end, and a detent between the rigid member end and the module operable to releasably secure the module at the predetermined position thereof on the rigid member end with the pin refracted away from the bone.

10. A bone fixation apparatus comprising:

at least one elongate bone pin having a proximal end and a distal bone gripping end;

an external pin positioner member for supporting the pin in gripping engagement with a bone from external of a patient's body; and a pin advancing mechanism mounted to the positioner member having an opening through which the pin extends for being shifted with coarse adjustments into advanced positions of the pin and into engagement with a bone upon application of manual force to the pin proximal end, and an adjustment device which allows for fine adjustments to be made to the advanced positions of the pin for fine tuning of engagement forces between the pin and bone so that the pin is secured to the bone with a two-stage application procedure.

11. The bone fixation apparatus of claim 10 wherein the pin advancing mechanism includes a housing with the opening for the pin formed therein, and the adjustment device is a screw member threaded in the opening for being advanced into the housing with turning thereof.

12. A bone fixation apparatus comprising:

at least one elongate bone pin having a proximal end and a distal bone gripping end;

an external pin positioner member for supporting the pin in gripping engagement with a bone from external of a patient's body; and a pin advancing mechanism mounted to the positioner member having an opening through which the pin extends for being shifted into advanced positions of the pin and into engagement with a bone upon application of manual force to the pin proximal end, and an adjustment device which allows for fine adjustments to be made to the advanced positions of the pin for fine tuning of engagement forces between the pin and bone;

wherein the advancing mechanism comprises a ratchet assembly to provide coarse adjustments to the pin advanced positions and which is substantially fixed to the pin upon removal of manual force therefrom, and the fine adjustment device comprises a screw device for being turned and advanced into engagement with the ratchet assembly to fine tune the advanced position of the pin.

13. The bone fixation apparatus of claim 12 wherein the advancing mechanism includes a housing fixed to the positioner member and having the opening which receives the screw device threaded therein, the housing further having a slot, and the ratchet assembly includes a follower that is engaged by the screw member with turning thereof for being advanced in the slot, the slot having a predetermined length to define a predetermined amount of fine tune adjustment for the pin.

14. A bone fixation apparatus comprising:

at least one elongate bone pin having a proximal end and a distal bone gripping end;

an external pin positioner member for supporting the pin in gripping engagement with a bone from external of a patient's body; and a pin advancing mechanism mounted to the positioner member having an opening through which the pin extends for being shifted into advanced positions of the pin and into engagement with a bone upon application of manual force to the pin proximal end, and an adjustment device which allows for fine adjustments to be made to the advanced positions of the pin for fine tuning of engagement forces between the pin and bone; and wherein the advancing mechanism includes a release member and a plurality of teeth along the bone pin with the release member biased with a predetermined bias force into engagement with the teeth to keep the advanced pin from retracting away from the bone.

15. The bone fixation apparatus of claim 14 wherein the release member includes one of a button that is shifted in a linear direction against the bias force and a lever that is pivoted against the bias force to allow the pin to be advanced into engagement with a bone.

16. A bone fixation apparatus comprising:

a plurality of bone pins;

a pair of pin positioner members each supporting at least one bone pin and having arcuately configured bodies;

an adjustable connection between the arcuate bodies to allow the pins supported thereby to be angularly shifted about an axis of an elongate bone for obtaining different angles of orientation to the bone with the bodies generally being adjusted in a single plane transverse to the bone axis so that the bodies extend in a substantially continuous arcuate configuration from a free end of one of the bodies to a free end of the other body; and pin holders attached to the bodies in which the pins are carried for being advanced into gripping engagement with the bone.

17. The bone fixation apparatus of claim 16 wherein the adjustable connection comprises a plurality of spaced apertures along at least one of the positioner bodies and a connecting member mounted to the other positioner body for being secured in a selected one of the spaced apertures.

18. The bone fixation apparatus of claim 17 wherein the adjustable connection comprises a set of spaced apertures along both of the positioner bodies with the apertures in at least one of the sets being threaded and the connecting member being a threaded fastener.

19. The bone fixation apparatus of claim 16 wherein the adjustable connection comprises a tongue and groove on respective positioner bodies for guiding sliding movement of the bodies between different connected positions relative to each other.

20. The bone fixation apparatus of claim 16 wherein the bodies have a predetermined cross-sectional configuration that is other than flat to increase the moment of inertia and strength thereof.

21. The bone fixation apparatus of claim 20 wherein one of the bodies has a generally U-shaped cross-sectional configuration and the other body has a generally T-shaped cross-sectional configuration.

22. The bone fixation apparatus of claim 16 wherein the pin holders are releasably connected to one of the ends of each of the pin positioner bodies, the adjustable connection allows the bodies to be detached from one another, and one of the pin positioner bodies includes a pin opening at an opposite end to the one thereof for removably receiving a pin fixed therein with the bodies detached from each other.

23. The bone fixation apparatus of claim 16 wherein the pin holders are modules carrying one or multiple bone pins with the modules releasable connected to one of the ends of each of the positioner bodies.

* * * * *

UNITED STATES PATENT AND TRADEMARK OFFICE
CERTIFICATE OF CORRECTION

PATENT NO. : 6,860,883 B2
DATED : March 1, 2005
INVENTOR(S) : Janowski et al.

It is certified that error appears in the above-identified patent and that said Letters Patent is hereby corrected as shown below:

Column 21,
Line 16, after "mechanism" insert -- including --, therefor.
Line 23, delete "advances" and insert -- advance --, therefor.

Column 22,
Line 8, delete "tripping" and insert -- gripping --.
Line 28, delete "refracted" and insert -- retracted --, therefor.

Signed and Sealed this

Twelfth Day of July, 2005

JON W. DUDAS
*Director of the United States Patent and Trademark Office*